(12) United States Patent
Lee et al.

(10) Patent No.: US 11,325,101 B2
(45) Date of Patent: May 10, 2022

(54) SUPER ABSORBENT POLYMER AND METHOD FOR PREPARING THE SAME

(71) Applicant: LG Chem, Ltd., Seoul (KR)

(72) Inventors: Sang Gi Lee, Daejeon (KR); Hye Mi Nam, Daejeon (KR); Min Ho Hwang, Daejeon (KR); Soo Jin Lee, Daejeon (KR); Tae Hwan Jang, Daejeon (KR)

(73) Assignee: LG Chem, Ltd.

( * ) Notice: Subject to any disclaimer, the term of this patent is extended or adjusted under 35 U.S.C. 154(b) by 1023 days.

(21) Appl. No.: 15/556,740

(22) PCT Filed: Nov. 17, 2016

(86) PCT No.: PCT/KR2016/013286
§ 371 (c)(1),
(2) Date: Sep. 8, 2017

(87) PCT Pub. No.: WO2017/146347
PCT Pub. Date: Aug. 31, 2017

(65) Prior Publication Data
US 2018/0050321 A1 Feb. 22, 2018

(30) Foreign Application Priority Data

Feb. 25, 2016 (KR) .................. 10-2016-0022849
Aug. 12, 2016 (KR) .................. 10-2016-0103023

(51) Int. Cl.
| | | |
|---|---|---|
| A61K 35/50 | (2015.01) | |
| A61K 33/24 | (2019.01) | |
| B01J 20/26 | (2006.01) | |
| C08J 3/24 | (2006.01) | |
| C08F 2/26 | (2006.01) | |
| C08F 20/18 | (2006.01) | |
| C08F 6/00 | (2006.01) | |
| A61L 15/60 | (2006.01) | |
| C08K 5/20 | (2006.01) | |
| B01J 20/30 | (2006.01) | |
| C08F 220/06 | (2006.01) | |
| B01J 20/10 | (2006.01) | |
| B01J 20/28 | (2006.01) | |
| C08F 20/14 | (2006.01) | |
| C08K 3/36 | (2006.01) | |

(52) U.S. Cl.
CPC ............ *B01J 20/267* (2013.01); *A61L 15/60* (2013.01); *B01J 20/103* (2013.01); *B01J 20/265* (2013.01); *B01J 20/28004* (2013.01); *B01J 20/3021* (2013.01); *B01J 20/3064* (2013.01); *B01J 20/3078* (2013.01); *B01J 20/3085* (2013.01); *C08F 2/26* (2013.01); *C08F 6/008* (2013.01); *C08F 20/14* (2013.01); *C08F 20/18* (2013.01); *C08F 220/06* (2013.01); *C08J 3/245* (2013.01); *C08K 3/36* (2013.01); *C08K 5/20* (2013.01); *B01J 2220/68* (2013.01); *C08J 2333/02* (2013.01)

(58) Field of Classification Search
CPC .. B01J 20/267; B01J 20/103; B01J 20/28004; B01J 20/3021; B01J 20/3085; C08F 20/14; C08J 3/245; C08K 3/26; A61L 15/50
USPC ........................................................ 502/402
See application file for complete search history.

(56) References Cited

U.S. PATENT DOCUMENTS

| | | |
|---|---|---|
| 4,883,478 A | 11/1989 | Lerailler et al. |
| 4,973,632 A | 11/1990 | Nagasuna et al. |
| 5,032,628 A | 7/1991 | Choi et al. |
| 5,118,719 A | 6/1992 | Lind |
| 5,328,935 A | 7/1994 | Van Phan et al. |
| 5,563,218 A | 10/1996 | Rebre et al. |
| 5,712,316 A | 1/1998 | Dahmen et al. |
| 5,985,944 A | 11/1999 | Ishizaki et al. |
| 6,107,358 A | 8/2000 | Harada et al. |
| 6,133,193 A | 10/2000 | Kajikawa et al. |
| 6,174,929 B1 | 1/2001 | Hahnle et al. |
| 6,414,214 B1 | 7/2002 | Engelhardt et al. |
| 6,565,768 B1 | 5/2003 | Dentler et al. |
| 6,750,262 B1 | 6/2004 | Hahnle et al. |
| 7,638,570 B2 | 12/2009 | Torii et al. |
| 7,803,880 B2 * | 9/2010 | Torii ................... C08F 20/06 525/329.7 |
| 2001/0038831 A1 | 11/2001 | Park et al. |
| 2004/0019342 A1 | 1/2004 | Nagasuna et al. |
| 2004/0214946 A1 | 10/2004 | Smith et al. |
| 2005/0054784 A1 | 3/2005 | Qin et al. |
| 2005/0137546 A1 | 6/2005 | Joy et al. |
| 2005/0256469 A1 | 11/2005 | Qin et al. |
| 2006/0204755 A1 | 9/2006 | Torii et al. |
| 2007/0066167 A1 | 3/2007 | Wada et al. |

(Continued)

FOREIGN PATENT DOCUMENTS

| | | |
|---|---|---|
| CN | 1856331 A | 11/2006 |
| CN | 101094696 A | 12/2007 |

(Continued)

OTHER PUBLICATIONS

Riehm et al., Langmuir, (2016), v32, p. 3954-3962.*

(Continued)

*Primary Examiner* — Yong L Chu
(74) *Attorney, Agent, or Firm* — Lerner, David, Littenberg, Krumholz & Mentlik, LLP

(57) ABSTRACT

The present invention relates to a super absorbent polymer having not only excellent absorption rate and absorbency under load but also excellent rewetting properties, and a method for preparing the same.

10 Claims, 4 Drawing Sheets

(56) References Cited

U.S. PATENT DOCUMENTS

| | | |
|---|---|---|
| 2007/0123658 A1 | 5/2007 | Torii et al. |
| 2007/0141338 A1 | 6/2007 | Ishizaki et al. |
| 2008/0058747 A1 | 3/2008 | Singh Kainth et al. |
| 2008/0139693 A1 | 6/2008 | Ikeuchi et al. |
| 2008/0161499 A1 | 7/2008 | Riegel et al. |
| 2008/0215026 A1 | 9/2008 | Schornick et al. |
| 2008/0234645 A1 | 9/2008 | Dodge et al. |
| 2009/0196848 A1 | 8/2009 | Davis |
| 2010/0057027 A1 | 3/2010 | Furno et al. |
| 2010/0099781 A1 | 4/2010 | Tian et al. |
| 2011/0204288 A1 | 8/2011 | Funk et al. |
| 2011/0313113 A1 | 12/2011 | Sakamoto et al. |
| 2012/0045639 A1 | 2/2012 | Whitmore et al. |
| 2012/0184670 A1 | 7/2012 | Kobayashi et al. |
| 2012/0184684 A1 | 7/2012 | Funk et al. |
| 2012/0219728 A1 | 8/2012 | Badri et al. |
| 2012/0232177 A1 | 9/2012 | Lopez Villanueva et al. |
| 2012/0258851 A1 | 10/2012 | Nakatsuru et al. |
| 2012/0296296 A1 | 11/2012 | Di Cintio et al. |
| 2012/0296297 A1 | 11/2012 | Di Cintio et al. |
| 2012/0296298 A1 | 11/2012 | Gray et al. |
| 2012/0296299 A1 | 11/2012 | Villanueva et al. |
| 2012/0309619 A1 | 12/2012 | Kwon et al. |
| 2013/0102750 A1 | 4/2013 | Watanabe et al. |
| 2013/0172180 A1 | 7/2013 | Naumann et al. |
| 2014/0066584 A1 | 3/2014 | Peterson et al. |
| 2014/0127510 A1 | 5/2014 | Handa et al. |
| 2014/0296423 A1 | 10/2014 | Ebata et al. |
| 2014/0306155 A1 | 10/2014 | Tian et al. |
| 2014/0306156 A1 | 10/2014 | Tian et al. |
| 2014/0312273 A1* | 10/2014 | Wattebled ............... A61L 15/24 252/194 |
| 2014/0364824 A1 | 12/2014 | Ota et al. |
| 2015/0011388 A1 | 1/2015 | Matsumoto et al. |
| 2015/0087742 A1 | 3/2015 | Won et al. |
| 2015/0093575 A1 | 4/2015 | Naumann et al. |
| 2015/0129799 A1 | 5/2015 | Kobayashi et al. |
| 2015/0137546 A1 | 5/2015 | Gaudig |
| 2015/0198339 A1 | 7/2015 | Jeon |
| 2015/0283284 A1 | 10/2015 | Azad et al. |
| 2016/0108227 A1 | 4/2016 | Wattebled et al. |
| 2016/0151531 A1 | 6/2016 | Lee et al. |
| 2016/0184799 A1 | 6/2016 | Lee et al. |
| 2018/0037686 A1 | 2/2018 | Lee et al. |
| 2018/0050321 A1 | 2/2018 | Lee et al. |
| 2018/0056274 A1 | 3/2018 | Lee et al. |
| 2018/0079847 A1 | 3/2018 | Lee et al. |
| 2018/0265645 A1 | 9/2018 | Nam et al. |
| 2018/0265646 A1 | 9/2018 | Nam et al. |

FOREIGN PATENT DOCUMENTS

| | | |
|---|---|---|
| CN | 101133100 A | 2/2008 |
| CN | 102197057 A | 9/2011 |
| CN | 102666670 A | 9/2012 |
| CN | 102762616 A | 10/2012 |
| CN | 103179931 A | 6/2013 |
| CN | 104024291 A | 9/2014 |
| CN | 104284921 A | 1/2015 |
| CN | 104603159 A | 5/2015 |
| EP | 0555692 A1 | 8/1993 |
| EP | 0615736 A1 | 9/1994 |
| EP | 0644211 A1 | 3/1995 |
| EP | 0744435 A1 | 11/1996 |
| EP | 1400556 A1 | 3/2004 |
| EP | 1637105 A1 | 3/2006 |
| EP | 1730218 B1 | 12/2010 |
| EP | 3248990 A1 | 11/2017 |
| EP | 3260485 A1 | 12/2017 |
| EP | 2797566 B1 | 6/2019 |
| JP | H06313042 A | 11/1994 |
| JP | H09124879 A | 5/1997 |
| JP | H10139916 A | 5/1998 |
| JP | H10251309 A | 9/1998 |
| JP | H11071425 A | 3/1999 |
| JP | H11156188 A | 6/1999 |
| JP | 2005154758 A | 6/2005 |
| JP | 2006116535 A | 5/2006 |
| JP | 20070012623 A | 1/2007 |
| JP | 3913867 B2 | 5/2007 |
| JP | 2007314794 A | 12/2007 |
| JP | 2009227885 A | 10/2009 |
| JP | 2011511086 A | 4/2011 |
| JP | 5336704 B2 | 11/2013 |
| JP | 2014098172 A | 5/2014 |
| JP | 2014514128 A | 6/2014 |
| JP | 2014514432 A | 6/2014 |
| JP | 2014518716 A | 8/2014 |
| JP | 2014523452 A | 9/2014 |
| JP | 2015503655 A | 2/2015 |
| JP | 2015150059 A | 8/2015 |
| JP | 2015213911 A | 12/2015 |
| KR | 910008293 B1 | 10/1991 |
| KR | 930077272 B1 | 8/1993 |
| KR | 100269980 B1 | 10/2000 |
| KR | 20050022813 A | 3/2005 |
| KR | 20060015498 A | 2/2006 |
| KR | 20060023116 A | 3/2006 |
| KR | 20090042828 A | 4/2009 |
| KR | 20090123904 A | 12/2009 |
| KR | 20110092236 A | 8/2011 |
| KR | 20120102088 A | 9/2012 |
| KR | 20130120300 A | 11/2013 |
| KR | 20140054324 A | 5/2014 |
| KR | 20140056225 A | 5/2014 |
| KR | 20140094536 A | 7/2014 |
| KR | 20140095569 A | 8/2014 |
| KR | 20140102264 A | 8/2014 |
| KR | 20140107347 A | 9/2014 |
| KR | 20150016126 A | 2/2015 |
| KR | 20150040476 A | 4/2015 |
| KR | 20150084371 A | 7/2015 |
| KR | 20150116418 A | 10/2015 |
| KR | 20150143624 A | 12/2015 |
| KR | 101582241 B1 | 1/2016 |
| KR | 20160010517 A | 1/2016 |
| WO | 87003208 A1 | 6/1987 |
| WO | 2004096304 A1 | 11/2004 |
| WO | 2005092956 A1 | 10/2005 |
| WO | 2006069732 A1 | 7/2006 |
| WO | 2011026876 A1 | 3/2011 |
| WO | 2013099174 A1 | 7/2013 |
| WO | 2014167040 A1 | 10/2014 |
| WO | 2014168858 A1 | 10/2014 |
| WO | 2014168871 A1 | 10/2014 |

OTHER PUBLICATIONS

Third Party Observation for Application No. EP16890123.9 dated Jul. 10, 2018.
Third Party Observation for Application No. PCT/KR2016/013286 dated Jun. 25, 2018.
Kabiri, K., et al.., "Novel approach to highly porous superabsorbent hydrogels: synergistic effect of porogens on porosity and swelling rate." Polymer International, vol. 52, Jan. 7, 2003, pp. 1158-1164.
Kabiri, Kourosh, et al. "Porous Superabsorbent Hydrogel Composites: Synthesis, Morphology and Swelling Rate." Macromolecular Materials and Engineering, Apr. 20, 2004, vol. 289, pp. 653-661.
Odian, George, "Principle of Polymerization." Second Edition, (Wiley, 1981), p. 203.
Schwalm, Reinhold, "UV Coatings: Basics, Recent Developments and New Applications." Elservier Science, Dec. 21, 2016, p. 115.
Search report from International Application No. PCT/KR2016/003793, dated Dec. 22, 2016.
Search report from International Application No. PCT/KR2016/003946, dated Jul. 29, 2016.
Search report from International Application No. PCT/KR2016/003948, dated Jul. 27, 2016.
Search report from International Application No. PCT/KR2016/005809, dated Aug. 24, 20116.

(56) References Cited

OTHER PUBLICATIONS

Search report from International Application No. PCT/KR2016/013286, dated Mar. 6, 2017.
U.S. Appl. No. 15/554,852, filed Aug. 31, 2017.
U.S. Appl. No. 15/556,078, filed Sep. 6, 2017.
U.S. Appl. No. 15/556,083, filed Sep. 6, 2017.
U.S. Appl. No. 15/558,429, filed Sep. 14, 2017.
Third Party Observation for Application No. PCT/KR2016/003946 dated Oct. 31, 2017.
Third Party Observation for Application No. PCT/KR2016/003948 dated Oct. 13, 2017.
Third Party Observation for PCT/KR2016/005809 dated Sep. 29, 2017.
Extended European Search Report including Written Opinion for Application No. EP16890123.9 dated Sep. 7, 2018.
Lee at al., U.S. Appl. No. 15/564,487, filed Oct. 5, 2017, titled "Super Absorbent Polymer".
Odian, George, "Principles of Polymerization." Second Edition, Copyright 1981, p. 203.
Schwalm, Reinhold, "UV Coatings: Basics, Recent Developments and New Applications." Elsevier Science, Dec. 21, 2006, p. 115.
Search report from International Application No. PCT/KR2016/006202, dated Sep. 12, 2016.
Extended European Search Report including Written Opinion for Application No. EP16803731.5 dated Sep. 3, 2018.
Extended European Search Report including Written Opinion for Application No. EP16811803.2 dated Aug. 27, 2018.
Third Party Observation for PCT/KR2016/006202 dated Oct. 16, 2017.
Extended European Search Report including Written Opinion for Application No. EP16835267.2 dated Aug. 22, 2018.
Third Party Observation for Application No. 16811871.9 dated Jan. 3, 2020, 7 pages.
Buchholz, et al., Modern Superabsorbent Polymer Technology, 1998, vol. 152, pp. 199-201, New York: Wiley-vch.
Third Party Observation for Application No. 16890123.9 dated Jan. 3, 2020, 4 pages.
Decision dated Dec. 15, 2003 of the Boards of Appeal of the European Patent Office for Application No. 92115510.7. (2003). 23 pgs.

* cited by examiner

[FIG. 1]
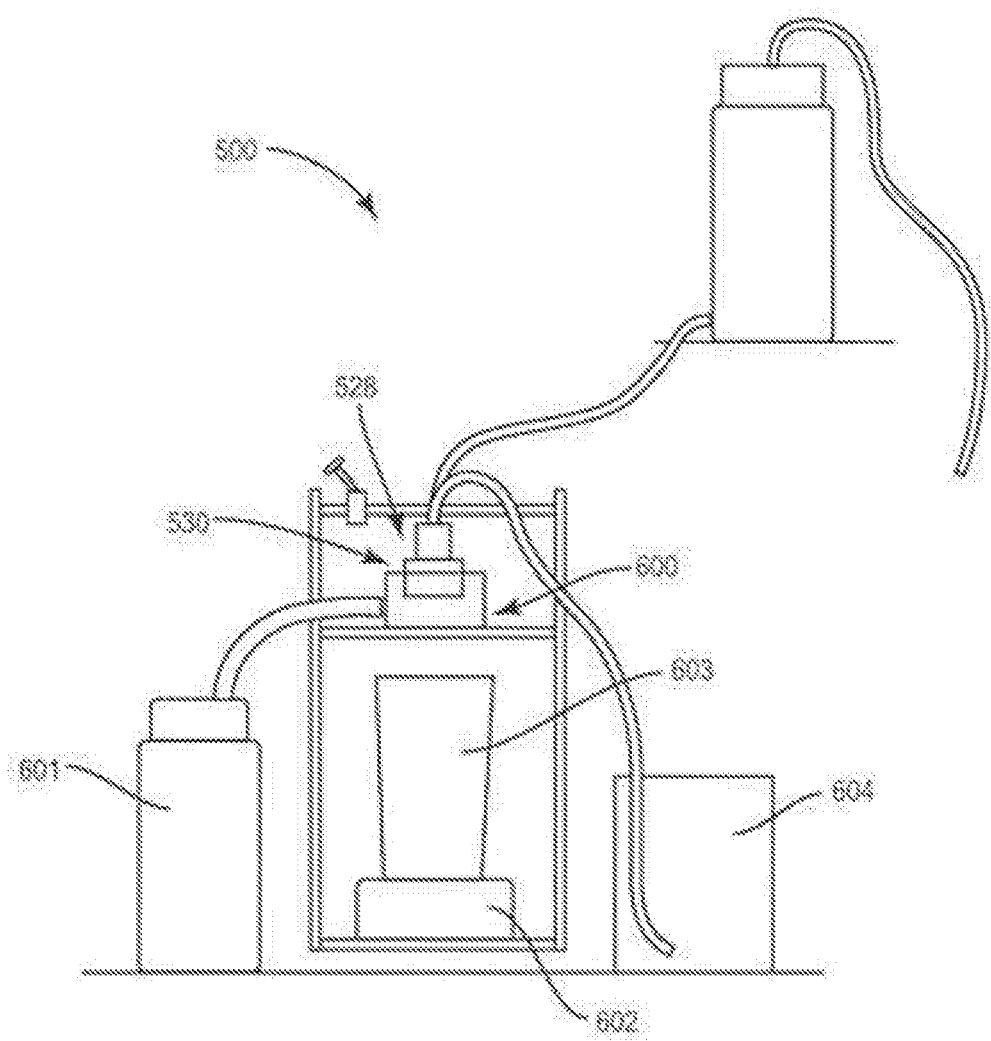

[FIG. 2]
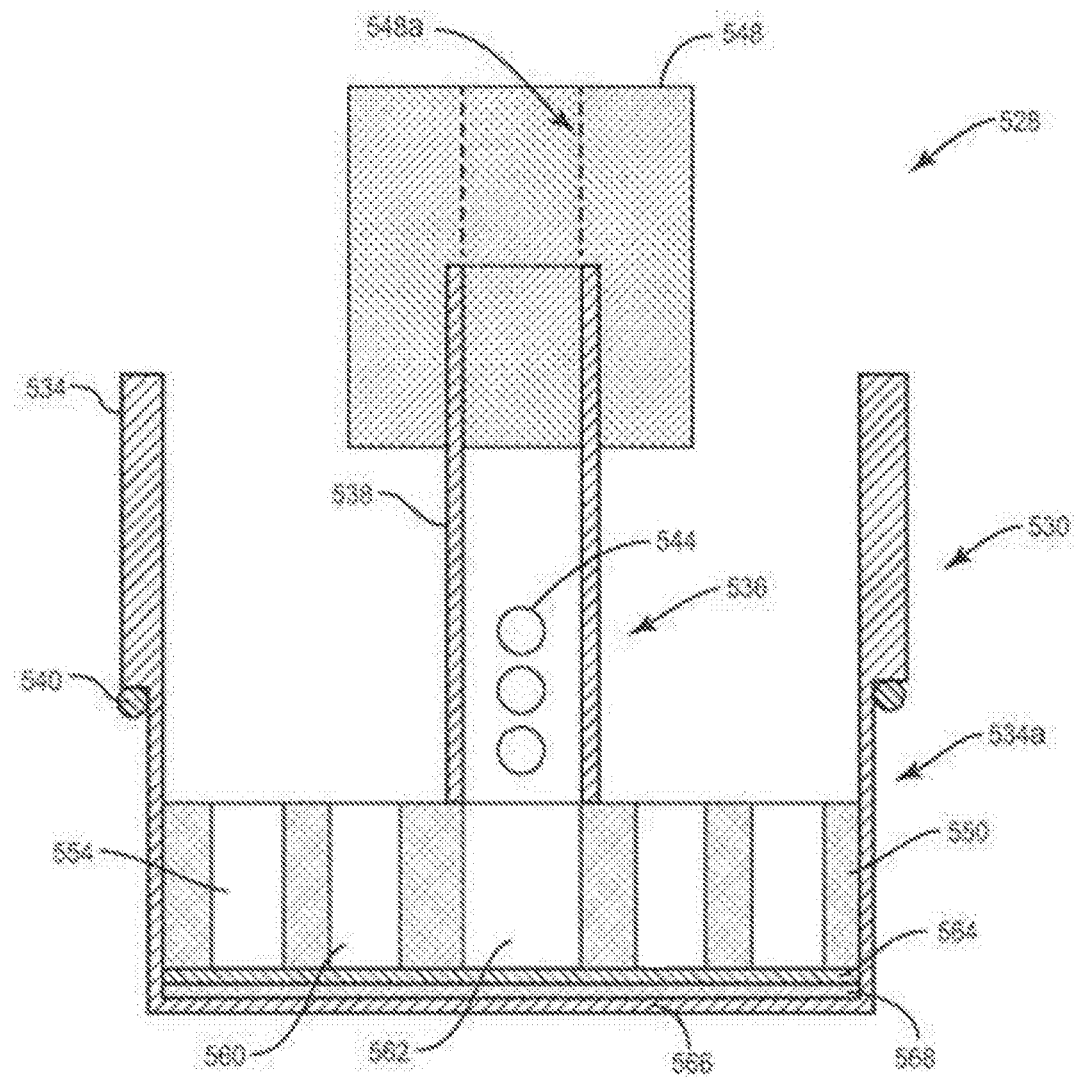

[FIG. 3]
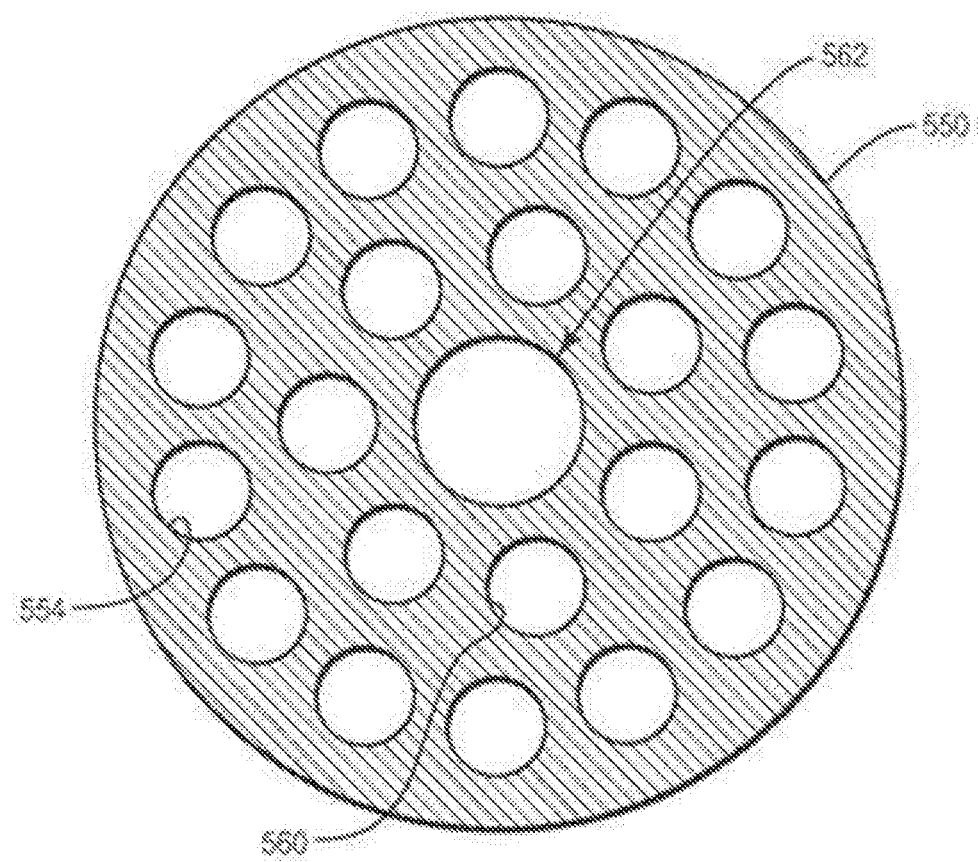

[FIG. 4]
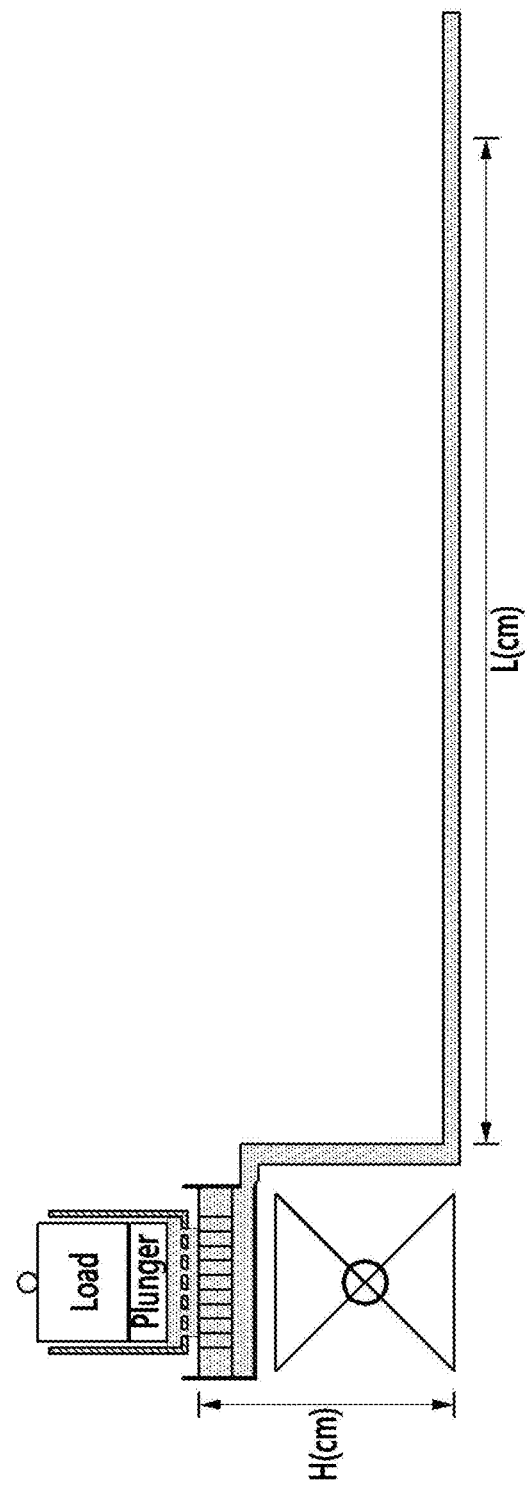

SUPER ABSORBENT POLYMER AND METHOD FOR PREPARING THE SAME

CROSS-REFERENCE TO RELATED APPLICATION(S)

The present application is a national phase entry under 35 U.S.C. § 371 of International Application No. PCT/KR2016/013286 filed Nov. 17, 2016, published in Korean, which claims priority from Korean Patent Application No. 10-2016-0022849 filed Feb. 25, 2016 and Korean Patent Application No. 10-2016-0103023 filed Aug. 12, 2016, all of which are incorporated herein by reference.

TECHNICAL FIELD

The present invention relates to a super absorbent polymer having not only excellent vortex time and absorbency under load but also excellent rewetting properties.

BACKGROUND OF ART

Super absorbent polymer (SAP) is a synthetic polymer material capable of absorbing moisture from about 500 to about 1,000 times its own weight, and each manufacturer has denominated it as different names such as SAM (Super Absorbency Material), AGM (Absorbent Gel Material) or the like. Such super absorbent polymers started to be practically applied in sanitary products, and now they are widely used for preparation of various products, for example, hygiene products such as paper diapers for children or sanitary napkins, water retaining soil products for gardening, water stop materials for the civil engineering and construction, sheets for raising seedling, fresh-keeping agents for food distribution fields, materials for poultice or the like.

In most cases, these super absorbent polymers have been widely used in the field of hygienic materials such as diapers or sanitary napkins. For these applications, the super absorbent polymer should exhibit a high moisture absorbency, it should not release the absorbed water even in the external pressure, and additionally it should well retain the shape even in a state where the volume is expanded (swelled) by absorbing water, and thereby exhibit excellent liquid permeability.

However, it is known that it is difficult to improve both a centrifuge retention capacity (CRC), which is the physical property showing the basic absorption capacity and the water retaining capacity of the super absorbent polymer, and an absorbency under load (AUL), which shows the properties of well retaining the absorbed moisture even under the external pressure. This is because, when the overall crosslinking density of the super absorbent polymer is controlled to be low, the absorbency can be relatively high, but the crosslinking structure may be loose, the gel strength may be low and thus the absorbency under load may be lowered. On the contrary, when controlling the crosslink density to a high level to improve the absorbency under load, it becomes difficult for moisture to be absorbed between densely crosslinked structures, so that the basic centrifuge retention capacity may be lowered. For the reasons described above, there is a limitation in providing a super absorbent polymer having improved centrifuge retention capacity and improved absorbency under load together.

However, recently, as hygiene materials such as a diaper or a sanitary napkin become thinner, super absorbent polymers are required to have higher absorption performance. Among these, improving both a centrifuge retention capacity and an absorbency under load which are conflicting physical properties, improving a liquid permeability, and so on, have become an important task.

In addition, pressure can be applied to hygiene materials such as diapers or sanitary napkins due to the weight of the user. In particular, when a super absorbent polymer applied to sanitary materials such as diapers or sanitary napkins absorbs liquid and then pressure is applied due to the weight of the user, a rewetting phenomenon where some liquid absorbed in the super absorbent polymer again release out can occur. Accordingly, various attempts have been made to improve the absorbency under load and the liquid permeability in order to suppress such rewetting phenomenon. However, concrete methods capable of effectively suppressing the rewetting phenomenon have not been suggested.

DETAILED DESCRIPTION OF THE INVENTION

Technical Problem

For resolving the aforesaid problems of the prior arts, it is an object of the present invention to provide a super absorbent polymer having not only excellent vortex time and absorbency under load but also excellent rewetting properties. Specifically, the present invention provides a super absorbent polymer having improved rewetting properties of a diaper by improving the ability of the super absorbent polymer to absorb water from the wet pulp in the absorbent core of the diaper when hygiene products such as a diaper are exposed to urine or the like. In addition, it is another object of the present invention to provide a method for preparing the above-described super absorbent polymer.

Technical Solution

In order to achieve these objects, the present invention provides a super absorbent polymer comprising:

a base polymer powder containing a first crosslinked polymer of a water-soluble ethylene-based unsaturated monomer having an acidic group in which at least a part thereof is neutralized; and a surface-crosslinked layer containing a second crosslinked polymer formed on the base polymer powder in which the first crosslinked polymer is additionally crosslinked via a surface crosslinking agent, wherein the super absorbent polymer has:
an average particle diameter of 300 μm to 600 μm,
CRC of 28 g/g or more,
AUL (0.9 psi) of 18 g/g or more,
10-min WAUL of 15 g/g or more,
a gel bed permeability (GBP) for a physiological saline solution of 30 darcy or more,
5-min Gel-Vacuum AUL of 18 g/g or more, and
a vortex time of 50 seconds or less.

The present invention also provides a super absorbent polymer comprising:

a base polymer powder containing a first crosslinked polymer of a water-soluble ethylene-based unsaturated monomer having an acidic group in which at least a part thereof is neutralized; and a surface-crosslinked layer containing a second crosslinked polymer formed on the base polymer powder in which the first crosslinked polymer is additionally crosslinked via a surface crosslinking agent, wherein the first crosslinked polymer is a porous polymer containing a plurality of pores on a micron (μm) scale, and wherein the super absorbent polymer has an average particle size of 300 μm to 600 μm, CRC of 28 g/g or more, AUL (0.9 psi) of 18 g/g or more, 5-min Gel-Vacuum AUL of 18 g/g or more, and a vortex time of 50 seconds or less.

A super absorbent polymer applied to a sanitary product such as a diaper has a problem that, when the polymer is in contact with urine and is mostly absorbed, but urine which is not sufficiently absorbed leaks to the surface of the super absorbent polymer due to the weight of the user or the like. The phenomenon that some liquid absorbed in the super absorbent polymer again leaks out is called a rewetting phenomenon. In order to improve such rewetting, attempts have been made to increase the absorbency under load and to improve the liquid permeability, but they have reached a satisfactory level.

After the lapse of a certain period of time after the diaper has absorbed urine, if urine is again leaked from the super absorbent polymer, from the water contained in the pulp, or from the water remaining in the diaper sub-material, it cause a deterioration in the rewetting. Among them, especially when a certain weight of pressure is applied to the wet pulp (due to water contained in the pulp), water's leaking out has the greatest effect on re-wetting.

In order to minimize this problem, the ability of the diaper not to extrude water even under pressure after the lapse of a certain period of time after exposed to urine, i.e., a suction capacity or a wicking ability which is the ability of the super absorbent polymer to attract water from the wet pulp under pressure, is very important. Particularly, since the rewetting is mainly a characteristic under load, the suction capacity under pressure is very important.

In the present invention, in order to evaluate the suction capacity under pressure, the suction capacity of the super absorbent polymer under pressure through a capillary tube was analyzed. In this way, in order to increase the suction capacity under pressure, it is necessary that the super absorbent polymer should have a porous structure and the pore size is controlled to a certain size or less so that the capillary phenomenon can occur.

Therefore, the present invention has a feature that, by using a carbonate foaming agent and an anionic surfactant at the time of polymerization of the super absorbent polymer, the properties of the super absorbent polymer are enhanced and the rewetting phenomenon is suppressed to a satisfactory level, as will be described later.

Preferably, the first crosslinked polymer is a porous polymer that is subjected to expanded polymerization and contains a plurality of pores with micron (μm) scale. Here, the average diameter of the pores is preferably 100 μm or less. More preferably, the average diameter of the pores is 90 μm or less, 80 μm or less, or 70 μm or less, or 35 μm or more, or 40 μm or more.

In the present invention, the extent of the rewetting phenomenon can be measured by WAUL (wicking absorbency under load) and can be specifically obtained by the following Equation 1:

$$WAUL(g/g) = [W_2(g) - W_1(g)] / W_0(g) \qquad \text{[Equation 1]}$$

in Equation 1, $W_0(g)$ is an initial weight(g) of the super absorbent polymer, $W_1(g)$ is the total sum of a weight of the super absorbent polymer and a weight of the device capable of providing a load to the super absorbent polymer, $W_2(g)$ is the total sum of a weight of the super absorbent polymer and a weight of the device capable of providing a load to the super absorbent polymer, after absorbing a physiological saline solution below 15 cm from the super absorbent polymer under a load (0.7 psi) for 10 minutes.

Specifically, WAUL is measured using a measuring apparatus as shown in FIG. 4. A filter paper is placed on a Kit having a hole at the bottom and sucking up water from the bottom, and AUL Kit (1 inch in diameter) is placed on it. A tube through which a physiological saline solution under a height (H) of 15 cm from the super absorbent polymer is supplied is connected to the Kit. Specifically, a tube with an inner diameter of 0.19 mm is horizontally connected, and the filter paper is placed on the Kit, which has a hole at the bottom at a height of 15 cm and can suck up water from the bottom, and the AUL Kit is placed on it. 0.16 g of a super absorbent polymer sample previously classified to a diameter of 300 to 600 μm is weighed. After evenly spreading on the bottom, the absorbency of salt water is measured under a condition that a load of 0.7 psi is applied.

After measuring WAUL, the suction capacity of salt water through the capillary tube is measured and simultaneously the ability to pull the salt water up at a constant height can be evaluated. This can be defined as an analytical method capable of representatively showing the wicking ability of the super absorbent polymer, similarly to the ability of pulp to suck water. WAUL increases with the time of absorption of a physiological saline solution, indicating a trend similar to AUL. In the present invention, WAUL after absorption for 10 minutes was used as an evaluation standard.

Preferably, the WAUL is 12.0 g/g or more, 13.0 g/g or more, or 14.0 g/g or more. In addition, the higher the value of WAUL, the more excellent it is. Thus, the upper limit thereof is not limited, but as an example, it may be 25 g/g or less, 24 g/g or less, 23 g/g or less, 22 g/g or less, 21 g/g or less, or 20 g/g or less.

Moreover, the super absorbent polymer according to the present invention has a vortex time of 50 seconds or less, which is excellent. The vortex time is a physical property for evaluating the swelling rate of the super absorbent polymer, and it can be calculated by measuring the amount of time required until the vortex disappears after adding 2 g of the super absorbent polymer to 50 mL of physiological saline and then stirring the mixture at 600 rpm.

Preferably, the super absorbent polymer according to the present invention has a vortex time of 45 seconds or less, 40 seconds or less, or 35 seconds or less. Also, the smaller the vortex time, the more excellent it is. Thus, the lower limit thereof may be 0 seconds or more, 5 seconds or more, 10 seconds or more, 15 seconds or more, 20 seconds or more, 25 seconds or more, or 30 seconds or more.

In addition, the super absorbent polymer according to the present invention has a gel bed permeability (GBP) for a physiological saline solution of 30 darcy or more, which is excellent.

The gel bed permeability (GBP) for a physiological saline solution can be measured in units of Darcy or $cm^2$ according to the following method described in Korean Patent Application No. 10-2014-7018005. One Darcy means that it permits a flow of 1 $cm^3$/s of a fluid with viscosity of 1 cP under a pressure gradient of 1 atm/cm through an area of 1 $cm^2$. The gel bed permeability has the same units as area and one darcy is equal to $0.98692 \times 10^{-12}$ $m^2$, or $0.98692 \times 10^{-8}$ $cm^2$.

More specifically, in this specification, GBP means a penetration (or permeability) of a swollen gel layer (or bed) under conditions referred to as 0 psi free swell state (a Gel Bed Permeability (GBP) Under 0 psi Swell Pressure Test), and the GBP can be measured using the apparatus shown in FIGS. 1 to 3.

Referring to FIGS. 1-3, the test apparatus assembly 528 in a device 500 for measuring GBP includes a sample container 530 and a plunger 536. The plunger includes a shaft 538 having a cylinder hole bored down the longitudinal axis and a head 550 positioned at the bottom of the shaft. The shaft hole 562 has a diameter of about 16 mm. The plunger head is attached to the shaft, for example, by an adhesive. Twelve holes 544 are bored into the radial axis of the shaft, and three positioned at every 90 degrees having diameter of about 6.4 mm. The shaft 538 is machined from a LEXAN rod or equivalent material, and has an outer diameter of about 2.2 cm and an inner diameter of about 16 mm. The plunger head 550 has seven inner holes 560 and fourteen outer holes 554, all holes having a diameter of about 8.8 mm. Further, a hole of about 16 mm is aligned with the shaft. The plunger head 550 is machined from a LEXAN rod or equivalent material and has a height of about 16 mm and a diameter sized such that it fits within the cylinder 534 with minimum wall clearance but still moves freely. The total length of the plunger head 550 and shaft 538 is about 8.25 cm, but can be machined at the top of the shaft to obtain the desired size of the plunger 536. The plunger 536 includes a 100 mesh stainless steel cloth screen 564 that is biaxially stretched to tautness and attached to the lower end of the plunger 536. The screen is attached to the plunger head 550 using a suitable solvent that causes the screen to be securely adhered to the plunger head 550. Care should be taken to avoid excess solvent moving into the openings of the screen and reducing the open area for liquid flow area. Acrylic solvent Weld-on 4 from IPS Corporation (having a place of business in Gardena, Calif., USA) can be used appropriately. The sample container 530 includes a cylinder 534 and a 400 mesh stainless steel cloth screen 566 that is biaxially stretched to tautness and attached to the lower end of the plunger 534. The screen is attached to the cylinder using a suitable solvent that causes the screen to be securely adhered to the cylinder. Care should be taken to avoid excess solvent moving into the openings of the screen and reducing the open area for liquid flow. Acrylic solvent Weld-on 4 from IPS Corporation (having a place of business in Gardena, Calif., USA) can be used appropriately. The gel particle sample (swollen super absorbent polymer), indicated as 568 in FIG. 2, is supported on the screen 566 within the cylinder 534 during testing.

Cylinder 534 may be bored from a transparent LEXAN rod or equivalent material, or it may be cut from LEXAN tubing or equivalent material, and has an inner diameter of about 6 cm (for example, a cross sectional area of about 28.27 cm$^2$), a wall thickness of about 0.5 cm and a height of about 7.95 cm. A step can be formed by machining into the outer diameter of the cylinder 534 such that a region 534$a$ having an outer diameter of 66 mm is present at the bottom 31 mm of the cylinder 534. An O-ring 540 which fits the diameter of the region 534$a$ may be placed on top of the step.

The annular weight 548 has a counter-bored hole of about 2.2 cm in diameter and 1.3 cm deep so it slides freely onto the shaft 538. The annular weight also has a thru-bore 548$a$ of about 16 mm. The annular weight 548 may be made from stainless steel or from other suitable material capable of corrosion resistance in 0.9% by weight of physiological saline solution (aqueous sodium chloride solution). The combined weight of the plunger 536 and the annular weight 548 is equal to about 596 g, which corresponds to a pressure applied to the sample 568 of about 0.3 psi or about 20.7 dyne/cm$^2$ (2.07 kPa), over a sample area of about 28.27 cm$^2$.

When the test solution flows through the test apparatus during testing of the GBP, the sample container 530 generally rests on a weir 600. The purpose of the weir is to divert liquid that overflows the top of the sample container 530, and diverts the overflow liquid to a separate collection device 601. The weir can be positioned above a scale 602 with a beaker 603 resting on it to collect a physiological saline solution passing through the swollen sample 568.

In order to perform the gel bed permeability test under "free swell" conditions, the plunger 536 installed with the weight 548 is placed in an empty sample container 530, and the height from the top of the weight 548 to the bottom of the sample container 530 is measured to an accuracy of 0.01 mm using an appropriate gauge. The force to which the thickness gauge applies during the measurement should be as low as possible, preferably less than about 0.74 N. When using multiple test apparatus, it is important to keep each empty sample container 530, plunger 536 and weight 548 and track of which they are used. Further, it is preferable that the base on which the sample container 530 is placed is flat, and the surface of the weight 548 is parallel to the bottom surface of the sample container 530. Then, a sample to be tested is prepared from the super absorbent polymer for measuring GBP. As an example, a test sample is prepared from a super absorbent polymer having a particle diameter of about 300 to about 600 µm, which is passed through a US standard 30 mesh screen and retained on a US standard 50 mesh screen. About 2.0 g of a sample is placed in a sample container 530 and spread out evenly on the bottom of the sample container. The container containing 2.0 g of sample, without the plunger 536 and the weight 548 therein, is then submerged in the 0.9 wt % physiological saline solution for about 60 minutes and allow the sample to swell under no load condition. At this time, the sample container 530 is placed on the mesh located in a liquid reservoir so that the sample container 530 is raised slightly above the bottom of the liquid reservoir. As the mesh, those which do not affect the movement of the physiological saline solution into the sample container 530 can be used. As such mesh, part number 7308 from Eagle Supply and Plastic (having a place of business in Appleton, Wis., USA) can be used. During saturation, the height of the physiological saline solution can be adjusted such that the surface within the sample container is defined by the sample, rather than the physiological saline solution.

At the end of this period, the assembly of the plunger 536 and weight 548 is placed on the saturated sample 568 in the sample container 530 and then the sample container 530, plunger 536, weight 548 and sample 568 are removed from the solution. Thereafter, before GBP measurement, the sample container 530, plunger 536, weight 548 and sample 568 are placed on a flat, large grid non-deformable plate of uniform thickness for about 30 seconds. The plate will prevent liquid in the sample container from being released onto a flat surface due to surface tension. The plate has an overall dimension of 7.6 cm×7.6 cm, and each grid has a dimension of 1.59 cm long×1.59 cm wide×1.12 cm deep. A suitable plate material is a parabolic diffuser panel, catalogue number 1624K27, available from McMaster Carr Supply Company (having a place of business in Chicago, Ill., USA), which can then be cut to the proper dimensions.

Then, if the zero point has not changed from the initial height measurement, the height from the top of the weight 548 to the bottom of the sample container 530 is measured again by using the same thickness gauge as previously used. The height measurement should be made as soon as practicable after the thickness gauge is installed. The height measurement obtained from measuring the empty sample container 530, plunger 536, and weight 548 is subtracted from the height measurement obtained after saturating the sample 568. The resulting value is the thickness, or height "H" of the saturated sample 568. Further, if a plate is contained in the assembly containing the saturated sample 568, the height including the plate should be measured even when measuring the height of the empty assembly.

The GBP measurement is started by delivering a flow of 0.9% physiological saline solution into the sample container 530 containing the saturated sample 568, the plunger 536 and the weight 548. The flow rate of physiological saline solution into the container is adjusted to cause physiological saline solution to overflow the top of the cylinder 534, thereby resulting in a consistent head pressure equal to the height of the sample container 530. The physiological saline solution may be added by any suitable means that is sufficient to ensure a small, but consistent amount of overflow from the top of the cylinder, such as with a metering pump 604. The overflow liquid is diverted into a separate collection device 601. The quantity of solution passing through the sample 568 versus time is measured gravimetrically using the scale 602 and beaker 603. Data points from the scale 602 are collected every second for at least 60 seconds once the overflow has started. Data collection may be taken manually or with data collection software. The flow rate (Q) passing through the swollen sample 568 is determined in units of grams/second (g/s) by a linear least-square fit of fluid passing through the sample 568 (in grams) versus time (in seconds).

Using the data thus obtained, the gel bed permeability can be confirmed by calculating the GBP (cm$^2$) according to the following Equation 2.

$$K=[Q \times H \times \mu]/[A \times \rho \times P] \quad \text{[Equation 2]}$$

in Equation 2,
K is a gel bed permeability (cm$^2$),
Q is a flow rate (g/sec)
H is a height of swollen sample (cm),
μ is a liquid viscosity (poise) (about 1 cP for the test solution used with this Test),
A is a cross-sectional area for liquid flow (28.27 cm$^2$ for the sample container used with this Test),
ρ is a liquid density (g/cm$^3$) (about 1 g/cm$^3$, for the test solution used with this Test), and
P is a hydrostatic pressure (dyne/cm$^2$) (normally about 7,797 dynes/cm$^2$).

The hydrostatic pressure is calculated from P=ρ×g×h, where ρ is a liquid density (g/cm$^3$), g is a gravitational acceleration (nominally 981 cm/sec$^2$), and h is a fluid height (for example, 7.95 cm for the GBP Test described herein)

In addition, the super absorbent polymer according to the present invention has a centrifuge retention capacity (CRC) for a physiological saline solution of 28 g/g or more which is excellent. The centrifuge retention capacity (CRC) for a physiological saline solution can be measured according to EDANA (European Disposables and Nonwovens Association) recommended test method No. WSP 241.2. More specifically, the CRC is obtained in accordance with the following Equation, after classifying a super absorbent polymer and preparing a super absorbent resin having a particle diameter of 300 μm to 600 μm, and absorbing the same in physiological saline solution for 30 minutes:

$$CRC(g/g)=\{[W_4(g)-W_3(g)]/W_0(g)\}-1 \quad \text{[Equation 3]}$$

in Equation 3,
$W_0(g)$ is an initial weight(g) of the super absorbent polymer having a particle diameter of 300 μm to 600 μm,
$W_3(g)$ a weight of the device not including the super absorbent polymer, measured after dehydrating the same by using a centrifuge at 250 G for 3 minutes, and
$W_4(g)$ is a weight of the device including a super absorbent polymer, measured after soaking and absorbing the super absorbent polymer having a particle diameter of 300 μm to 600 μm in 0.9 wt % physiological saline solution at room temperature for 30 minutes, and then dehydrating the same by using a centrifuge at 250 G for 3 minutes.

Further, the higher the value of CRC, the more excellent it is. Thus, the upper limit thereof is not limited, but as an example, it may be 35 g/g or less or 34 g/g or less.

Moreover, the super absorbent polymer according to the present invention has an absorbency under load (AUL) for a physiological saline solution (0.9 psi) of 18 g/g or more, which is excellent. The absorbency under load (AUL) (0.9 psi) can be measured according to EDANA recommended test method No. WSP 241.2. More specifically, the absorbency under load can be calculated in accordance with the following Equation 4, after absorbing the super absorbent polymer in a physiological saline solution under a load of about 0.9 psi over 1 hour:

$$AUL(g/g)=[W_6(g)-W_5(g)]/W_0(g) \quad \text{[Equation 4]}$$

in Equation 4,
$W_0(g)$ is an initial weight(g) of the super absorbent polymer,
$W_5(g)$ is the total sum of a weight of the super absorbent polymer and a weight of the device capable of providing a load to the super absorbent polymer, and
$W_6(g)$ is the total sum of a weight of the super absorbent polymer and a weight of the device capable of providing a load to the super absorbent polymer, after absorbing a physiological saline solution to the super absorbent polymer under a load (0.9 psi) for 1 hour.

$W_0(g)$ described in Equations 3 and 4 corresponds to an initial weight(g) of the super absorbent polymer, before absorbing a physiological saline solution to the super absorbent polymer, and they may be the same or different from each other.

Further, the higher the value of AUL, the more excellent it is. Thus, the upper limit thereof is not limited, but as an example, it may be 25 g/g or less or 24 g/g or less.

In addition, the super absorbent polymer according to the present invention has an average diameter of pores of 100 μm or less. Preferably, the average diameter of the pores is 90 μm or less, 80 μm or less, or 70 μm or less, or 35 μm or more, or 40 μm or more.

Further, the super absorbent polymer according to the present invention has 5-min Gel-Vacuum AUL of 18 g/g or more, which is excellent. The 5-min Gel-Vacuum AUL can be calculated by the following Equation 5:

$$\text{5-min Gel-Vacuum AUL}(g/g)=[W_8(g)-W_7(g)]/W_0(g) \quad \text{[Equation 5]}$$

in Equation 5,
$W_0(g)$ is an initial weight(g) of the super absorbent polymer,
$W_7(g)$ is the total sum of a weight of the super absorbent polymer and a weight of the device capable of providing a load to the super absorbent polymer, and
$W_8(g)$ is the total sum of a weight of the super absorbent polymer and a weight of the device capable of providing a load to the super absorbent polymer, measured after absorbing a physiological saline solution to the super absorbent polymer under a load (0.3 psi) for 5 minutes, and then removing the remaining liquid with a vacuum device.

Specifically, a physiological saline solution is absorbed to the super absorbent polymer under a load of about 0.3 psi over 5 minutes. Then, the remaining liquid which is not absorbed by the super absorbent resin is removed under vacuum. At this time, the remaining liquid not absorbed between the super absorbent polymer particles is removed, and the liquid absorbed by the super absorbent polymer is not removed under vacuum. According to the 5-min Gel-Vacuum AUL measurement method, the remaining liquid that may exist between the super absorbent polymer particles does not affect the measured value unlike the conventional method of measuring the absorbency under load, thereby more clearly evaluating the absorbency under load of the super absorbent polymer.

Further, the 5-minute Gel-Vacuum AUL is superior as the value is higher. Thus, the upper limit thereof is not limited, but it may be 25 g/g or less, or 24 g/g or less.

Further, the super absorbent polymer according to the present invention has a rewetting amount of 1 g/g or less. The rewetting amount can be calculated according to the following Equation 6:

$$\text{Rewetting Amount } (g/g) = [W_{10}(g) - W_9(g)] / W_0(g) \quad \text{[Equation 6]}$$

in Equation 6, $W_0(g)$ is an initial weight(g) of the super absorbent polymer, $W_9(g)$ is an initial weight(g) of the second filter paper, $W_{10}(g)$ is a weight(g) of the second filter paper that has absorbed a liquid leaking out from the super absorbent polymer swelled for 2 minutes under a load (0.7 psi), after the super absorbent polymers have absorbed 25 times their weight in a physiological saline solution for a sufficient time under no load condition.

Specifically, a super absorbent polymer having a particle diameter of 300 to 600 µm which is passed through a U.S. standard 30 mesh screen and retained on a U.S. standard 50 mesh screen is prepared from a super absorbent polymer for evaluating the rewetting properties. Meanwhile, a 400 mesh stainless steel screen is attached to the bottom of a plastic cylinder having an inner diameter of 25 mm. Then, the test assembly is prepared by uniformly spraying the previously prepared super absorbent polymer $W_0$ (g, 0.16 g) on the screen at room temperature and 50% humidity.

Then, a first filter paper having a diameter of 25 mm is laid on PE dish having a diameter of 80 mm, and the test assembly is placed thereon. Thereafter, 4 g of 0.9 wt % physiological saline solution is injected around the test assembly, so that the super absorbent polymer can absorb the physiological saline solution under no load condition. When the physiological saline solution is completely absorbed by the super absorbent polymer, it is left for 10 minutes so that the super absorbent polymer swells sufficiently.

On the other hand, as Whatman Grade No. 4 filter paper, 10 sheets of filter papers having a diameter of 30 mm or more are overlapped to prepare a second filter paper. Then, the weight $W_9(g)$ of the second filter paper is measured. After removing the test assembly from the first filter paper, a piston capable of uniformly applying a load of 5.1 kPa (0.7 psi) onto the swollen super absorbent polymer is added. At this time, the piston is designed so that the outer diameter is slightly smaller than 25 mm and thus it can move freely up and down without any gap with the inner wall of the cylinder. Then, the test assembly to which the piston is added is placed on the previously prepared second filter paper. After lifting and removing the test assembly to which the piston has been added after 2 minutes, the weight $W_{10}(g)$ of the second filter paper is again measured. The rewetting amount (g/g) is calculated by Equation 6 using each of the weights thus obtained.

On the other hand, the lower the value of the rewetting amount, the more excellent it is. Thus, the lower limit thereof may be theoretically 0 g/g, 0.05 g/g or more and 0.1 g/g or more.

In addition, the present invention provides a method of preparing a super absorbent polymer described above, which comprises the steps of:

1) performing thermal polymerization or photopolymerization of a monomer composition comprising a water-soluble ethylene-based unsaturated monomer having an acidic group in which at least a part thereof is neutralized, a carbonate forming agent, an anionic surfactant and a polymerization initiator to form a hydrogel polymer, 2) drying the hydrogel polymer, 3) pulverizing the dried polymer, and 4) performing surface crosslinking reaction of the pulverized polymer.

Hereinafter, the above preparation method will be described in detail for each step.

Step of Forming a Hydrogel Polymer (Step 1)

First, the method for preparing a super absorbent polymer includes a step of performing thermal polymerization or photopolymerization of a monomer composition comprising a water-soluble ethylene-based unsaturated monomer having an acidic group in which at least a part thereof is neutralized, and a polymerization initiator to form a hydrogel polymer.

The water-soluble ethylene-based unsaturated monomer contained in the monomer composition may be any monomer conventionally used in the production of a super absorbent polymer. As a non-limiting example, the water-soluble ethylene-based unsaturated monomer may be a compound represented by the following Chemical Formula 1:

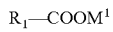

$$R_1\text{—COOM}^1 \quad \text{[Chemical Formula 1]}$$

In Chemical Formula 1, $R_1$ is an alkyl group having 2 to 5 carbon atoms containing an unsaturated bond, and $M^1$ is a hydrogen atom, a monovalent or divalent metal, an ammonium group or an organic amine salt.

Preferably, the monomer may be at least one selected from the group consisting of acrylic acid, methacrylic acid, and monovalent metal salts, divalent metal salts, ammonium salts, and organic amine salts of these acids. When an acrylic acid or a salt thereof is used as the water-soluble ethylene-based unsaturated monomer, it is advantageous because a super absorbent polymer having improved water absorptivity can be obtained. In addition, the above-mentioned monomer used herein may include maleic anhydride, fumaric acid, crotonic acid, itaconic acid, 2-acryloyl ethane sulfonic acid, 2-methacryloyl ethane sulfonic acid, 2-(meth)acryloyl propane sulfonic acid, 2-(meth)acrylamide-2-methylpropane sulfonic acid, (meth)acrylamide, N-substituted (meth)acrylate, 2-hydroxyethyl(meth)acrylate, 2-hydroxypropyl (meth)acrylate, methoxypolyethyleneglycol(meth)acrylate, polyethyleneglycol(meth)acrylate, (N,N)-dimethylaminoethyl(meth)acrylate, (N,N)-dimethylaminopropyl(meth)acrylamide, or the like.

Here, the water-soluble ethylene-based unsaturated monomer may have an acidic group, in which at least a part of the acidic group is neutralized. Preferably, those in which the monomer is partially neutralized with an alkaline substance such as sodium hydroxide, potassium hydroxide, ammonium hydroxide or the like can be used.

At this time, the degree of neutralization of the monomer may be 40 to 95 mol %, or 40 to 80 mol %, or 45 to 75 mol %. The range of the degree of neutralization may vary depending on the final physical properties. However, an excessively high degree of neutralization causes the neutralized monomers to be precipitated, and thus polymerization may not readily occur, whereas an excessively low degree of neutralization not only greatly deteriorates the absorbency of the polymer but also endows the polymer with hard-to-handle properties, like elastic rubber.

Further, the concentration of the water-soluble ethylene-based unsaturated monomer in the monomer composition can be appropriately adjusted in consideration of the polymerization time and reaction conditions, and may be preferably 20 to 90% by weight, or 40 to 65% by weight. Such a concentration range may be advantageous for adjusting the pulverization efficiency at the time of pulverization of the polymer as described below, while it is not required to remove the unreacted monomer after polymerization by using a gel effect phenomenon occurring in the polymerization reaction of the high concentration aqueous solution. However, when the concentration of the monomer is too low, the yield of the super absorbent polymer can be lowered. By contrast, when the concentration of the monomer is too high, there may be problems on the process that some of the monomers may be deposited or the pulverizing efficiency of the prepared hydrogel polymer is reduced in the pulverizing process, and thus the properties of the super absorbent polymer may be lowered.

In addition, the monomer composition may include a polymerization initiator generally used in the production of a super absorbent polymer. As a non-limiting example, as the polymerization initiator, a thermal polymerization initiator, a photo-polymerization initiator or the like may be used depending on the polymerization method. However, even in the case of the photo-polymerization method, a certain amount of heat is generated by ultraviolet irradiation or the like, and a certain amount of heat is generated in accordance with the progress of the polymerization reaction, which is an exothermic reaction, and thus, a thermal polymerization initiator may further be included.

The photo-polymerization initiator used herein may include, for example, one or more compounds selected from the group consisting of benzoin ether, dialkyl acetophenone, hydroxyl alkyl ketone, phenyl glyoxylate, benzyl dimethyl ketal, acyl phosphine and a-aminoketone. Among them, as a specific example of the acylphosphine, a commonly used lucyrin TPO, that is, 2,4,6-trimethyl-benzoyl-trimethyl phosphine oxide may be used. More various photo-polymerization initiators are well disclosed in "UV Coatings: Basics, Recent Developments and New Application" written by Reinhold Schwalm, (Elsevier, 2007), p 115, the content of which is incorporated herein by reference.

Moreover, as thermal polymerization initiator, one or more compounds selected from the group consisting of a persulfate-based initiator, an azo-based initiator, hydrogen peroxide, and ascorbic acid may be used. Specific examples of the persulfate-based initiator may include sodium persulfate ($Na_2S_2O_8$), potassium persulfate ($K_2S_2O_8$), ammonium persulfate (($NH_4)_2S_2O_8$), and the like. In addition, examples of the azo-based initiator may include 2,2-azobis(2-amidinopropane)dihydrochloride, 2,2-azobis-(N,N-dimethylene) isobutyramidine dihydrochloride, 2-(carbamoylazo)isobutylonitril, 2,2-azobis[2-(2-imidazolin-2-yl)propane] dihydrochloride, 4,4-azobis-(4-cyanovaleric acid) or the like. More various thermal polymerization initiators are well disclosed in "Principle of Polymerization" written by Odian, (Wiley, 1981), p 203, the content of which is incorporated herein by reference.

The polymerization initiator may be included in a concentration of about 0.001% to 1% by weight based on the monomer composition. That is, when the concentration of the polymerization initiator is too low, the polymerization rate may become slow and a large amount of residual monomer may be extracted in the final product, which is not preferable. Conversely, when the concentration of the polymerization initiator is too high, the polymer chains constituting the network become short, and thus the content of water-soluble components is increased and physical properties of the polymer may deteriorate such as a reduction in absorbency under load, which is not preferable.

Meanwhile, the monomer composition may include a crosslinking agent ("internal crosslinking agent") to improve physical properties of the polymer by polymerization of the water-soluble ethylene-based unsaturated monomer. The crosslinking agent is used for internal crosslinking of the hydrogel polymer, and is used separately from a surface crosslinking agent described below.

As the internal crosslinking agent, any compound can be used as long as it enables introduction of crosslinkage upon polymerization of the water-soluble ethylene-based unsaturated monomers. Non-limiting examples of the internal crosslinking agent may include multifunctional crosslinking agents, such as N,N'-methylenebisacrylamide, trimethylolpropane tri(meth)acrylate, ethylene glycol di(meth)acrylate, polyethylene glycol(meth)acrylate, propylene glycol di(meth)acrylate, polypropylene glycol(meth)acrylate, butanediol di(meth)acrylate, butylene glycol di(meth)acrylate, diethylene glycol di(meth)acrylate, hexanediol di(meth)acrylate, allyl methacrylate, triethylene glycol di(meth)acrylate, tripropylene glycol di(meth)acrylate, tetraethylene glycol di(meth)acrylate, dipentaerythritol pentacrylate, glycerin tri (meth)acrylate, pentaerythritol tetraacrylate, triallylamine, ethylene glycol diglycidyl ether, propylene glycol, glycerin, or ethylene carbonate, which may be used alone or in combination of two or more thereof, but are not limited thereto.

The internal crosslinking agent may be added at a concentration of about 0.001% by weight to 1% by weight, based on the monomer composition. That is, if the concentration of the internal crosslinking agent is too low, the absorption rate of the polymer lowers and the gel strength may become weak, which is undesirable. Conversely, if the concentration of the internal crosslinking agent is too high, the absorption capacity of the polymer is lowered and thereby is not preferred for an absorbent.

Meanwhile, the monomer composition contains a carbonate foaming agent and an anionic surfactant in order to improve the properties of the super absorbent polymer.

The carbonate foaming agent serves to improve the properties of the super absorbent polymer by forming the inner pores of the hydrogel polymer during polymerization. Preferably, as the carbonate foaming agent, at least one selected from the group consisting of sodium carbonate, sodium hydrogen carbonate, magnesium carbonate, calcium carbonate, potassium carbonate, and potassium hydrogen carbonate may be used. Further, preferably, the carbonate foaming agent is used in an amount of 0.01 to 0.1% by weight relative to the water-soluble ethylene-based unsaturated monomer.

The anionic surfactant serves to induce a uniform distribution of the components in the monomer composition during polymerization and improve the properties of the super absorbent polymer. As the anionic surfactant, a carboxylic acid salt, a sulfonic acid salt, or a phosphate, containing 6 to 18 carbon atoms, may be preferably used. Specific examples thereof include sodium laurylsulfonate, potassium laurylsulfonate, sodium lauryl ethylene glycol sulfonate, potassium lauryl ethylene glycol sulfonate, sodium lauryl phosphate, potassium lauryl phosphate, sodium lauryl ethylene glycol phosphate, potassium lauryl ethylene glycol phosphate, sodium dioctylsulfonate, potassium dioctylsulfonate, sodium dioctylethylene glycol sulfonate, potassium dioctylethylene glycol sulfonate, and the like. Further, preferably, the anionic surfactant is used in an amount of 0.05 to 3% by weight relative to the water-soluble ethylene-based unsaturated monomer.

In addition, the monomer composition may further include an additive such as a thickener, a plasticizer, a preservation stabilizer, an antioxidant, etc., if necessary.

Further, these monomer compositions can be prepared in the form of a solution in which raw materials such as the above-described monomers, polymerization initiator, carbonate foaming agent, anionic surfactant, internal crosslinking agent, etc. are dissolved in a solvent.

In this case, as the solvent, any solvent may be used without limitations in the constitution as long as it is able to dissolve the above raw materials. Examples of the solvent may include water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, N,N-dimethylacetamide, or a mixture thereof.

The formation of the hydrogel polymer through polymerization of the monomer composition may be performed by a general polymerization method, and the process is not particularly limited. Non-limiting examples of the polymerization method are largely classified into thermal polymerization and the photo-polymerization according to the type of the polymerization energy source, and thermal polymerization may be carried out in a reactor like a kneader equipped with agitating spindles and the photo-polymerization may be carried out in a reactor equipped with a movable conveyor belt.

For example, the monomer composition is injected into a reactor like a kneader equipped with the agitating spindles, and thermal polymerization is performed by providing hot air thereto or heating the reactor, thereby obtaining the hydrogel polymer. In this case, the hydrogel polymer, which is discharged from the outlet of the reactor according to the type of agitating spindles equipped in the reactor, may be obtained as particles with a size of centimeters or millimeters. Specifically, the hydrogel polymer may be obtained in various forms according to the concentration of the monomer composition fed thereto, the feeding speed, or the like, and the hydrogel polymer having a (weight average) particle diameter of 2 mm to 50 mm may be generally obtained.

As another example, when the photo-polymerization of the monomer composition is performed in a reactor equipped with a movable conveyor belt, a sheet-shaped hydrogel polymer may be obtained. In this case, the thickness of the sheet may vary depending on the concentration of the monomer composition fed thereto and the feeding speed, and the polymer sheet is preferably controlled to have typically a thickness of 0.5 to 5 cm in order to secure the production speed or the like while uniformly polymerizing the entire sheet.

The hydrogel polymer formed by the above method may have a water content of about 40 to 80% by weight. The "water content" as used herein means a weight occupied by moisture with respect to a total weight of the hydrogel polymer, which may be the value obtained by subtracting the weight of the dried polymer from the weight of the hydrogel polymer. Specifically, the water content can be defined as a value calculated by measuring the weight loss due to evaporation of moisture in the polymer in the drying process by raising the temperature of the polymer through infrared heating. At this time, the drying conditions may be determined as follows: the drying temperature is increased from room temperature to about 180° C. and then the temperature may be maintained at 180° C., and the total drying time may be set to 20 minutes, including 5 minutes for the temperature rising step.

Step of Drying the Hydrogel Polymer (Step 2)

The hydrogel polymer obtained through the above-mentioned step is subjected to a drying step for imparting water absorbency. However, in order to increase the efficiency of such drying, a step of pulverizing (coarsely grinding) the hydrogel polymer may be first performed before the drying step.

As a non-limiting example, the pulverizing devices usable for the above coarse grinding include a vertical pulverizing device, a turbo cutter, a turbo grinder, a rotary cutter mill, a cutter mill, a disc mill, a shred crusher, a crusher, a chopper, and a disc cutter, and the like.

In this case, the coarse pulverization may be performed so that the hydrogel polymer has a particle diameter of 2 mm to 10 mm. That is, in order to increase the drying efficiency, the hydrogel polymer is preferably pulverized into particles of 10 mm or less. However, since a phenomenon of agglomeration between particles may occur during excessive pulverization, it is desirable that the hydrogel polymer is pulverized into particles of 2 mm or more.

Since the coarsely pulverizing step is performed in a state where the water content of the polymer is high, a phenomenon where the polymer adheres to the surface of the pulverizer may occur. In order to minimize such phenomenon, water, surfactant, agglomeration preventing agent (for example, clay, silica, etc.); persulfate-based initiators, azo-based initiators, hydrogen peroxide, thermal polymerization initiator, epoxy-based crosslinking agent, a diol crosslinking agent, a crosslinking agent containing difunctional, trifunctional or higher polyfunctional acrylate, crosslinking agent with mono-funtionality containing a hydroxyl group or the like can be added to the hydrogel polymer as needed.

Then, the step of drying the hydrogel polymer (or coarsely pulverized hydrogel polymer) obtained through the above-mentioned steps is included.

The drying may be carried out at a temperature of 120 to 250° C., or 150 to 200° C., or 160 to 180° C. (wherein the temperature can be defined as the temperature of a heat medium provided thereto for drying or the temperature inside the dry reactor containing the heat medium and the polymer in the drying process). In other words, when the drying temperature is low and thus the drying time becomes long, the physical properties of the final polymer may be deteriorated. In order to prevent this problem, the drying temperature is preferably 120° C. or more. In addition, when the drying temperature is higher than necessary, only the surface of the hydrogel polymer is dried and thus the generation of fine powder may increase in the pulverizing step described later, and the physical properties of the super absorbent polymer finally formed may be deteriorated. In order to prevent this problem, the drying temperature is preferably 250° C. or less.

At this time, the drying time in the drying step is not particularly limited, but it may be adjusted to 20 to 90 minutes under the above drying temperature in consideration of the process efficiency and the like.

Furthermore, any known drying method may be used in the drying step without limitation in the constitution if it can be generally used for drying the hydrogel polymer. Specifically, the drying step may be carried out by a method of supplying hot air, irradiating infrared rays, irradiating microwaves, irradiating ultraviolet rays or the like.

The polymer dried by the method described above may exhibit the water content of about 0.1 to 10% by weight. In other words, if the water content of the dried polymer is less than 0.1% by weight, production costs may be increased due to excessive drying and degradation of the crosslinked polymer may occur, which is not desirable. In addition, if the water content of the polymer is more than 10% by weight, defects may occur in a subsequent process, which is not desirable.

Step of Pulverizing the Dried Polymer (Step 3)

The method for preparing the super absorbent polymer includes the step of pulverizing the polymer dried through the above-mentioned steps.

The pulverization step is a step for optimizing the surface area of the dried polymer, and may be performed so that the particle diameter of the pulverized polymer is 150 to 850 μm. Examples of the pulverizers usable for pulverizing the polymer to such a particle size include a pin mill, a hammer mill, a screw mill, a roll mill, a disc mill, a jog mill or the like.

Further, in order to control the physical properties of the super absorbent polymer finally produced, the step of selectively classifying particles having a particle diameter of 150 to 850 μm in the polymer particles obtained through the above-mentioned pulverization step may be further performed.

Step of Performing Surface Crosslinking Reaction of the Pulverized Polymer (Step 4)

The method for preparing the super absorbent polymer includes a step of performing surface crosslinking reaction of the polymer pulverized through the above-mentioned steps.

The surface cross-linking is a method of increasing the cross-linking density of the surface of the polymer particle, and it can be performed by a method of mixing a solution containing a crosslinking agent (surface crosslinking agent) and the above pulverized polymer and performing a crosslinking reaction.

Here, the type of the crosslinking agent (surface crosslinking agent) contained in the surface crosslinking solution is not particularly limited. As a non-limiting example, the surface crosslinking agent may be at least one compound selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene carbonate, ethylene glycol, diethylene glycol, propylene glycol, triethylene glycol, tetraethylene glycol, propanediol, dipropylene glycol, polypropylene glycol, glycerin, polyglycerin, butanediol, heptanediol, hexanediol, trimethylolpropane, pentaerythritol, sorbitol, calcium hydroxide, magnesium hydroxide, aluminum hydroxide, iron hydroxide, calcium chloride, magnesium chloride, aluminum chloride and iron chloride.

At this time, the content of the surface crosslinking agent may be appropriately controlled according to the type of crosslinking agent, reaction conditions, etc., and may be preferably adjusted to 0.001 to 5 parts by weight based on 100 parts by weight of the pulverized polymer. If the content of the surface crosslinking agent is too low, the surface crosslinking may not be properly performed, and the physical properties of the final polymer may be deteriorated. Conversely, if the surface crosslinking agent is used in an excess amount, the absorption capacity of the polymer may rather decrease due to excessive surface crosslinking reaction, which is not preferable.

In addition, in the surface crosslinking step, the surface crosslinking reaction can be carried out by adding at least one inorganic substance selected from the group consisting of silica, clay, alumina, silica-alumina composite material, titania, zinc oxide and aluminum sulfate, in addition to the surface crosslinking agent. The inorganic material may be used in the form of powder or liquid, and in particular, it can be used as alumina powder, silica-alumina powder, titania powder, or nanosilica solution. Further, the inorganic material may be used in an amount of about 0.05 to about 2% by weight based on the total weight of the pulverized polymer.

Moreover, in the surface crosslinking step, as the surface crosslinking proceeds by adding a polyvalent metal cation in place of the inorganic substance or together with the inorganic substance, the surface crosslinking structure of the super absorbent polymer can be further optimized. This is presumably because such a metal cation can further reduce the crosslinking distance by forming a chelate with the carboxyl group (COOH) of the super absorbent polymer.

On the other hand, in order to carry out the surface crosslinking reaction step, a method of adding the surface crosslinking solution and the pulverized polymer to a reaction tank and mixing them, a method of spraying the surface crosslinking solution onto the pulverized polymer, a method of continuously supplying the pulverized polymer and the surface crosslinking solution and mixing them, or the like can be used.

Moreover, when adding the surface crosslinking solution, water may be further added. Adding water in this way may induce a more uniform dispersion of the crosslinking agent, prevent the aggregation phenomenon of the polymer powders, and further optimize the depth of penetration of the surface crosslinking agent to the polymer powders. In consideration of these objects and effects, the content of water to be added may be adjusted to 0.5 to 10 parts by weight based on 100 parts by weight of the pulverized polymer.

Then, the surface crosslinking reaction step can be carried out at a temperature of 100 to 250° C. and can be carried out continuously after the drying and pulverizing steps which proceed at a relatively high temperature. At this time, the surface crosslinking reaction can be carried out for 1 to 120 minutes, or 1 to 100 minutes, or 10 to 60 minutes. That is, in order to prevent the polymer particles from being damaged to thereby decrease their physical properties during excessive reaction while inducing the minimum surface crosslinking reaction, the surface crosslinking reaction may be carried out under the above-mentioned conditions.

Advantageous Effects

As described above, the super absorbent polymer according to the present invention has not only excellent vortex time and absorbency under load but also excellent rewetting properties, and thereby can be usefully used as a material for various sanitary articles.

BRIEF DESCRIPTION OF DRAWINGS

FIGS. 1 to 3 are schematic views of an exemplary apparatus for measuring the gel bed permeability and parts provided in the apparatus.

FIG. 4 is a schematic diagram of an exemplary apparatus for measuring WAUL.

DETAILED DESCRIPTION OF THE EMBODIMENTS

Hereinafter, preferred examples are presented to aid in understanding of the invention. However, the following examples are provided examples are provided for better understanding of the present invention, and the scope of the present invention is not limited thereto.

Example 1

A solution (Solution A) in which 11 g of 0.5% IRGA-CURE 819 initiator (110 ppm based on the monomer composition) diluted with acrylic acid and 28 g of 5% polyethylene glycol diacrylate (PEGDA, molecular weight 400) diluted with acrylic acid were mixed was prepared. Then, a solution (Solution B) of trimethylolpropane triacrylate containing 9 mol % of 5% ethylene oxide (Ethoxylated-TMPTA, TMP (EO) 9TA, M-3190 manufactured by Miwon Specialty Chemical Co., Ltd.) diluted with acrylic acid was prepared.

480 g of acrylic acid was injected into a 2 L glass reactor surrounded by a jacket through which a heat medium pre-cooled at 25° C. was circulated, and 37 g of the solution A and 14 g of the solution B were injected, respectively. Then, 700 g of 24% caustic soda solution (solution C) was slowly added dropwise to the glass reactor and mixed. After the temperature of the mixture increased to 72° C. or higher by neutralization heat upon dropwise addition of the solution C, the mixed solution was left until it was cooled. The degree of neutralization of acrylic acid in the mixed solution thus obtained was about 70 mol %.

Meanwhile, 5% sodium bicarbonate solution (solution D) diluted with water and 28 g of 4% sodium persulfate solution diluted with in water were dissolved to prepare a solution (solution E-1). Further, as a surfactant, 6.7 g of 4% DOSS (Dioctyl sodium sulfosuccinate) solution (solution E-2) diluted with water was prepared.

Then, when the temperature of the mixed solution was cooled to about 40° C., 14 g of the solution D previously prepared was injected into the mixed solution and mixed, and at the same time, the solution E-1 and the solution E-2 were injected.

Then, the above prepared solution was poured in a Vat-type tray (15 cm in width×15 cm in length) installed in a square polymerizer which had a light irradiation device installed at the top and was preheated to 80° C. Subsequently, the mixed solution was irradiated with light. It was confirmed that a gel was formed on the surface after about 20 seconds from light irradiation, and it was confirmed that polymerization reaction occurred simultaneously with foaming after about 30 seconds from light irradiation. Subsequently, the reaction was allowed for additional 2 minutes, and the polymerized sheet was taken out and cut into a size of 3 cm×3 cm. Then, the cut sheet was subjected to a crumb through a chopping process using a meat chopper to prepare crumbs.

The crumbs were then dried in an oven capable of shifting airflow up and down. The crumbs were uniformly dried by flowing hot air at 180° C. from the bottom to the top for 15 minutes and from the top to the bottom for 15 minutes, and thereby the dried product had a water content of 2% or less.

The dried product was pulverized using a pulverizer and classified to obtain a base polymer having a particle diameter of 150 to 850 μm. The base polymer thus prepared had a centrifuge retention capacity of 34.3 g/g and a water-soluble component content of 12.5% by weight. The centrifuge retention capacity was measured according to EDANA recommended test method No. WSP 241.2 and the water-soluble component content was measured according to EDANA WSP 270.2

Thereafter, 100 g of the base polymer was mixed with a crosslinking agent solution obtained by mixing 3 g of water, 3 g of methanol, 0.4 g of ethylene carbonate, and 0.5 g of Aerosil 200 (EVONIK), and then surface crosslinking reaction was carried out at 190° C. for 30 minutes. The resultant was pulverized and sieved to obtain a surface-linked super absorbent polymer having a particle size of 150 to 850 μm. To 100 g of the surface-linked super absorbent polymer thus obtained was added 0.1 g of Aerosil 200 (EVONIK) and dry mixed to obtain a desired super absorbent polymer.

Example 2

A super absorbent polymer was prepared in the same manner as in Example 1, except that the solution A was used in an amount of 34 g instead of 37 g, and 2.5 g of 5% allyl methacrylate solution diluted with acrylic acid was used instead of the solution B. The base polymer thus prepared had a centrifuge retention capacity of 34.6 g/g and a water-soluble component content of 12.1% by weight. The surface-crosslinked super absorbent polymer having a particle diameter of 150 to 850 μm was obtained in the same manner as in Example 1, by using the prepared base resin.

Example 3

A surface-crosslinked super absorbent polymer having a particle diameter of 150 to 850 μm was obtained in the same manner as in Example 2, except that 6.7 g of 4% SDS (sodium dodecyl sulfate) solution diluted with water was used as the solution E-2 in Example 2.

Example 4

A surface-crosslinked super absorbent polymer having a particle size of 150 to 850 μm was obtained in the same manner as in Example 3, except that 0.1 g of alumina (Alu 130, EVONIK) was added instead of 0.1 g of Aerosil 200 (EVONIK) in Example 3.

Comparative Example 1

A solution (Solution A) in which 11 g of 0.5% IRGA-CURE 819 initiator (110 ppm based on the monomer composition) diluted with acrylic acid and 54 g of 5% polyethylene glycol diacrylate (PEGDA, molecular weight 400) diluted with acrylic acid were mixed was prepared.

Then, 480 g of acrylic acid was injected into a 2 L glass reactor surrounded by a jacket through which a heat medium pre-cooled at 25° C. was circulated, and the solution A was injected. Then, 700 g of 24% caustic soda solution (solution C) was slowly added dropwise to the glass reactor and mixed. After the temperature of the mixture increased to 72° C. or higher by neutralization heat upon dropwise addition of the solution C, the mixed solution was left until it was cooled. The degree of neutralization of acrylic acid in the mixed solution thus obtained was about 70 mol %.

Meanwhile, 28 g of 4% sodium persulfate solution diluted with water were dissolved to prepare a solution (Solution E-1). Then, when the temperature of the mixed solution was cooled to about 40° C., the solution E-1 previously prepared was injected into the mixed solution.

The above prepared solution was then poured in a Vat-type tray (15 cm in width×15 cm in length) installed in a square polymerizer which had a light irradiation device installed at the top and was preheated to 80° C. Subsequently, the mixed solution was irradiated with light. It was confirmed that a gel was formed on the surface after about 20 seconds from light irradiation, and it was confirmed that polymerization reaction occurred simultaneously with foaming after about 30 seconds from light irradiation. Subsequently, the reaction was carried out for additional 2 minutes, and the polymerized sheet was taken out and cut into a size of 3 cm×3 cm. Then, the cut sheet was subjected to a chopping process using a meat chopper to prepare crumbs.

The crumbs were then dried in an oven capable of shifting airflow up and down. The crumbs were uniformly dried by flowing hot air at 180° C. from the bottom to the top for 15 minutes and from the top to the bottom for 15 minutes, and thereby the dried product had a water content of 2% or less.

The dried crumbs were pulverized using a pulverizer and classified to obtain a base polymer having a particle diameter of 150 to 850 μm. The base polymer thus prepared had a centrifuge retention capacity of 31.2 g/g and a water-soluble component content of 10.3% by weight. The centrifuge retention capacity was measured according to EDANA WSP 241.2 and the water-soluble component content was measured according to EDANA recommended test method No. WSP 270.2

Thereafter, 100 g of the base polymer was mixed with a crosslinking agent solution obtained by mixing 3 g of water, 3 g of methanol, 0.4 g of ethylene carbonate, and 0.5 g of Aerosil 200 (EVONIK), and then surface crosslinking reaction was carried out at 190° C. for 30 minutes. The resultant was pulverized and sieved to obtain a surface-linked super absorbent polymer having a particle diameter of 150 to 850 μm. To 100 g of the surface-crosslinked super absorbent polymer thus prepared was added 0.1 g of Aerosil 200 (EVONIK) and dry mixed to obtain a desired super absorbent polymer.

Comparative Example 2

A super absorbent polymer was obtained in the same manner as in Example 1, except that 5% sodium bicarbonate solution (solution D) diluted with water, and 4% DOSS (Dioctyl sodium sulfosuccinatesulfonate) solution (solution E-2) diluted with water as a surfactant were not used in Example 1.

Comparative Example 3

A super absorbent polymer was obtained in the same manner as in Example 1, except that 6.7 g of 4% DOSS (dioctyl sodium sulfosuccinate) solution (solution E-2) diluted with water was first mixed with acrylic acid before the addition of caustic soda (solution C).

Experimental Example: Evaluation of Physical Properties of Super Absorbent Polymer The physical properties of the super absorbent polymers prepared in Examples and Comparative Examples were evaluated by the following methods.

(1) WAUL (Wicking Absorbency Under Load)

WAUL was measured using a measuring apparatus as shown in FIG. 4. Specifically, a tube with an inner diameter of 0.19 mm was horizontally connected, and a filter paper is placed on Kit, which had a hole in the bottom at a height of 15 cm and thus could suck water up from the bottom, and the AUL Kit (diameter of 1 inch) was placed on it. 0.16 g ($W_0$) of a super absorbent polymer previously classified into a diameter of 300 to 600 μm is weighed. After evenly spreading on the bottom, a physiological saline solution was absorbed for 10 minutes under a condition that a load of 0.7 psi was applied. WAUL was calculated according to the following Equation 1:

$$\text{WAUL}(g/g) = [W_2(g) - W_1(g)] / W_0(g) \qquad \text{[Equation 1]}$$

In Equation 1, $W_0(g)$ is an initial weight(g) of the super absorbent polymer, $W_1(g)$ is the total sum of a weight of the super absorbent polymer and a weight of the device capable of providing a load to the super absorbent polymer, $W_2(g)$ is the total sum of a weight of the super absorbent polymer and a weight of the device capable of providing a load to the super absorbent polymer, after absorbing a physiological saline solution below 15 cm from the super absorbent polymer under a load (0.7 psi) for 10 minutes.

(2) Centrifuge Retention Capacity (CRC)

The centrifuge retention capacity (CRC) was measured according to EDANA recommended test method No. WSP 241.2.

Specifically, a super absorbent polymer having a particle diameter of 300 to 600 μm which was passed through a U.S. standard 30 mesh screen and retained on a U.S. standard 50 mesh screen was prepared from a super absorbent polymer for evaluating the centrifuge retention capacity. Then, the super absorbent polymer $W_0$ (g, about 0.2 g) having a particle diameter of 300 to 600 μm was uniformly placed into a nonwoven fabric-made bag, followed by sealing. Then, the bag was immersed into 0.9% by weight of physiological saline solution at room temperature. After 30 minutes, the bag was dehydrated at 250 G for 3 minutes with a centrifuge, and the weight $W_4(g)$ of the bag was then measured. Meanwhile, after carrying out the same operation using an empty bag not containing a super absorbent polymer, the weight $W_3(g)$ was measured.

Using the respective weights thus obtained, a centrifuge retention capacity was confirmed according to the following Equation 3:

$$\text{CRC}(g/g) = \{[W_4(g) - W_3(g)] / W_0(g)\} - 1 \qquad \text{[Equation 3]}$$

in Equation 3, $W_0(g)$ is an initial weight(g) of the super absorbent polymer having a particle diameter of 300 μm to 600 μm, $W_3(g)$ is a weight of the device not including the super absorbent polymer, measured after dehydrating the same by using a centrifuge at 250 G for 3 minutes, and $W_4(g)$ is a weight of the device including a super absorbent polymer, measured after soaking and absorbing the super absorbent polymer having a particle diameter of 300 μm to 600 μm in 0.9% by weight of physiological saline solution at room temperature for 30 minutes, and then dehydrating the same by using a centrifuge at 250 G for 3 minutes.

(3) Absorbency Under Load (AUL)

The absorbency under load (AUL) for a physiological saline solution (0.9 psi) was measured according to EDANA recommended test method No. WSP 242.2.

Specifically, a 400 mesh stainless steel net was attached to the bottom of a plastic cylinder having an inner diameter of 25 mm. $W_0$ (g, 0.16 g) of a super absorbent polymer for measuring the absorbency under load were uniformly scattered on the screen under conditions of room temperature and relative humidity of 50%. Then, a piston which could provide a load of 6.3 kPa (0.9 psi) uniformly was put thereon. At this time, the piston used was designed so that the outer diameter was slightly smaller than 25 mm and thus it could move freely up and down without any gap with the inner wall of the cylinder. Then, the weight $W_5$(g) of the device prepared in this way was measured. After putting a glass filter having a diameter of 90 mm and a thickness of 5 mm in a Petri dish having the diameter of 150 mm, 0.90% by weight of a physiological saline solution was poured in the dish. At this time, the physiological saline solution was poured until the surface level became equal to the upper surface of the glass filter. Then, a sheet of filter paper having a diameter of 90 mm was put on the glass filter. Subsequently, the prepared device was placed on the filter paper so that the super absorbent polymer in the device was swelled by a physiological saline solution under load. After one hour, the weight $W_6$(g) of the device containing the swollen super absorbent polymer was measured.

Using the weight thus measured, the absorbency under load was calculated according to the following Equation 4.

$$AUL(g/g)=[W_6(g)-W_5(g)]/W_0(g) \quad \text{[Equation 4]}$$

in Equation 4, $W_0$(g) is an initial weight(g) of the super absorbent polymer, $W_5$(g) is the total sum of a weight of the super absorbent polymer and a weight of the device capable of providing a load to the super absorbent polymer, and $W_6$(g) is the total sum of a weight of the super absorbent polymer and a weight of the device capable of providing a load to the super absorbent polymer, after absorbing a physiological saline solution to the super absorbent polymer under a load (0.9 psi) for 1 hour.

(4) Gel Bed Permeability (GBP)

The gel bed permeability (GBP) for a physiological saline solution was measured according to the following method described in Korean Patent Application No. 10-2014-7018005.

Specifically, the apparatus shown in FIGS. 1 to 3 was used to measure the free swell GBP. First, the plunger 536 installed with the weight 548 was placed in an empty sample container 530, and the height from the top of the weight 548 to the bottom of the sample container 530 was measured to an accuracy of 0.01 mm using an appropriate gauge. The force to which the thickness gauge applied during the measurement was adjusted to less than about 0.74 N.

Meanwhile, a super absorbent polymer having a particle diameter of about 300 to about 600 μm was obtained by selectively classifying a super absorbent polymer which was passed through a US standard 30 mesh screen and retained on a US standard 50 mesh screen.

About 2.0 g of the super absorbent polymer classified in this way was placed in the sample container 530 and spread out evenly on the bottom of the sample container. Then, the container not containing the plunger 536 and the weight 548 therein, was submerged in 0.9 wt % physiological saline solution for about 60 minutes and allowed the super absorbent polymer to swell under no load condition. At this time, the sample container 530 was placed on the mesh located in a liquid reservoir so that the sample container 530 was raised slightly above the bottom of the liquid reservoir. As the mesh, those which did not affect the movement of the physiological saline solution into the sample container 530 were used. During saturation, the height of the physiological saline solution could be adjusted such that the surface within the sample container was defined by the swollen super absorbent polymer, rather than the physiological saline solution.

At the end of this period, the assembly of the plunger 536 and weight 548 was placed on the swollen super absorbent polymer 568 in the sample container 530 and then the sample container 530, plunger 536, weight 548 and swollen super absorbent polymer 568 were removed from the solution. Thereafter, before GBP measurement, the sample container 530, plunger 536, weight 548 and swollen super absorbent polymer 568 were placed on a flat, large grid non-deformable plate of uniform thickness for about 30 seconds. The height from the top of the weight 548 to the bottom of the sample container 530 was measured again by using the same thickness gauge as previously used. Then, the height measurement value of the device in which the plunger 536 equipped with the weight 548 was placed in the empty sample container 530 was subtracted from the height measurement value of the device including the swollen super absorbent polymer 568, thereby obtaining the thickness or height "H" of the swollen super absorbent polymer.

For the GBP measurement, 0.9 wt % physiological saline solution was flowed into the sample container 530 containing the swollen super absorbent polymer 568, the plunger 536 and the weight 548. The flow rate of a physiological saline solution into the container was adjusted to cause the physiological saline solution to overflow the top of the cylinder 534, thereby resulting in a consistent head pressure equal to the height of the sample container 530. Then, the quantity of solution passing through the swollen super absorbent polymer 568 versus time was measured gravimetrically using the scale 602 and beaker 603. Data points from the scale 602 were collected every second for at least 60 seconds once the overflow has started. The flow rate (Q) passing through the swollen super absorbent polymer 568 was determined in units of grams/second (g/s) by a linear least-square fit of fluid passing through the sample 568 (in grams) versus time (in seconds).

Using the data thus obtained, the GBP ($cm^2$) was calculated according to the following Equation 3.

$$K=[Q \times H \times \mu]/[A \times \rho \times P] \quad \text{[Equation 3]}$$

in Equation 3,

K is a gel bed permeability ($cm^2$),

Q is a flow rate (g/sec)

H is a height of swollen super absorbent polymer (cm),

μ is a liquid viscosity (poise) (about 1 cP for the test solution used with this Test), A is a cross-sectional area for liquid flow (28.27 $cm^2$ for the sample container used with this Test), ρ is a liquid density ($g/cm^3$) (about 1 $g/cm^3$, for the physiological saline solution used with this Test), and P is a hydrostatic pressure (dynes/cm²) (normally about 7,797 dyne/cm²).

The hydrostatic pressure was calculated from P=ρ×g×h, where ρ is a liquid density (g/cm³), g is a gravitational acceleration (nominally 981 cm/sec²), and h is a fluid height (for example, 7.95 cm for the GBP Test described herein)

At least two samples were tested and the results were averaged to determine the free swell GBP of the super absorbent polymer, and the unit was converted to darcy (1 darcy=0.98692×10⁻⁸ cm²).

(5) Vortex Time

The vortex time of the super absorbent polymer was measured in the amount of time in seconds until the vortex disappeared after adding 2 g of a super absorbent polymer to 50 mL of physiological saline solution and then stirring the mixture at 600 rpm.

(6) 5-Min Gel-Vacuum AUL

The 400 mesh stainless steel screen was attached to the bottom of a plastic cylinder having an inner diameter of 25 mm. $W_0(g)$ of a super absorbent polymer for measuring the 5-min Gel-Vacuum AUL were uniformly scattered on the screen under conditions of room temperature and relative humidity of 50%. Then, a piston which could provide a load of 0.3 psi uniformly was put on the super absorbent polymer. At this time, the piston used was designed so that the outer diameter was slightly smaller than 25 mm and thus it could move freely up and down without any gap with the inner wall of the cylinder. Then, the weight $W_7(g)$ of the device prepared in this way was measured. After putting a glass filter having a diameter of 90 mm and a thickness of 5 mm in a Petri dish having the diameter of 150 mm, 0.9 wt % by weight of a physiological saline solution was poured in the dish. At this time, the physiological saline solution was poured until the surface level became equal to the upper surface of the glass filter. A sheet of filter paper having a diameter of 90 mm was put on the glass filter. Subsequently, the prepared device was placed on the filter paper so that the super absorbent polymer in the device was swelled by a physiological saline solution under load. After 5 minutes, the remaining liquid was removed using a vacuum pump. At this time, the remaining liquid not absorbed between the swollen super absorbent polymer particles was removed. The weight $W_g(g)$ of the device containing the super absorbent polymer was measured. Using the weight thus measured, the 5-min Gel-Vacuum AUL was calculated according to the following Equation 5.

$$\text{5-min Gel-Vacuum AUL } (g/g) = [W_8(g) - W_7(g)]/W_0(g) \quad \text{[Equation 5]}$$

in Equation 5, $W_0(g)$ is an initial weight(g) of the super absorbent polymer, $W_7(g)$ is the total sum of a weight of the super absorbent polymer and a weight of the device capable of providing a load to the super absorbent polymer, and $W_8(g)$ is the total sum of the weight of the super absorbent polymer and the weight of the device capable of providing a load to the super absorbent polymer, after absorbing a physiological saline solution to the super absorbent polymer under a load (0.3 psi) for 5 minutes and removing the remaining liquid with a vacuum device.

(7) Rewetting Properties

A super absorbent polymer having a particle diameter of 300 to 600 pm which was passed through a U.S. standard 30 mesh screen and retained on a U.S. standard 50 mesh screen was prepared from a super absorbent polymer for evaluating the rewetting properties. Meanwhile, the 400 mesh stainless steel screen was attached to the bottom of a plastic cylinder having an inner diameter of 25 mm. Then, $W_0$ (g, 0.16 g) of the previously prepared super absorbent polymer was uniformly scattered on the screen under conditions of room temperature and relative humidity of 50%, to thereby prepare a test assembly.

Then, a first filter paper having a diameter of 25 mm was laid on the PE dish having a diameter of 80 mm, and the test assembly was placed thereon. Thereafter, 4 g of 0.9 wt % physiological saline solution was injected around the test assembly, so that the super absorbent polymer could absorb the physiological saline solution under no load condition. When the physiological saline solution was completely absorbed by the super absorbent polymer, it was left for 10 minutes so that the super absorbent polymer was swollen sufficiently.

On the other hand, as Whatman Grade No. 4 filter paper, 10 sheets of filter papers having a diameter of 30 mm or more were overlapped to prepare a second filter paper. Then, the weight $W_5(g)$ of the second filter paper was measured. After lifting and removing the test assembly from the first filter paper, a piston capable of uniformly applying a load of 5.1 kPa (0.7 psi) onto the swollen super absorbent polymer was added. At this time, the piston was designed so that the outer diameter was slightly smaller than 25 mm and thus it could move freely up and down without any gap with the inner wall of the cylinder. Then, the test assembly to which the piston was added was placed on the previously prepared second filter paper. After lifting and removing the test assembly to which the piston has been added after 2 minutes, the weight $W_6(g)$ of the second filter paper was again measured. Using each of the weights thus obtained, the rewetting amount (g/g) was calculated by the Equation 4.

$$\text{Rewetting Amount } (g/g) = [W_6(g) - W_5(g)]/W_0(g) \quad \text{[Equation 4]}$$

in Equation 4, $W_0(g)$ is an initial weight(g) of the super absorbent polymer, $W_5(g)$ is an initial weight(g) of the second filter paper, $W_6(g)$ is a weight(g) of the second filter paper that has absorbed a liquid leaking out from the super absorbent polymer swelled for 2 minutes under a load (0.7 psi), after the super absorbent polymers have absorbed 25 times their weight in a physiological saline solution for a sufficient time under no load condition.

The results of the above measurement are shown in Table 1 below.

TABLE 1

|  | Average pore size(4 V/s)(μm) | CRC (g/g) | AUL (g/g) | WAUL (g/g) | Gel-AUL (g/g) | GBP (darcy) | Vortex time (s) | Rewetting amount (g/g) |
|---|---|---|---|---|---|---|---|---|
| Ex. 1 | 45 | 30.3 | 19.1 | 15.6 | 20.1 | 68 | 35 | 0.4 |
| Ex. 2 | 48 | 30.8 | 19.4 | 16.1 | 20.2 | 53 | 29 | 0.6 |
| Ex. 3 | 53 | 30.9 | 20.1 | 15.7 | 19.7 | 64 | 28 | 0.2 |
| Ex. 4 | 44 | 30.4 | 21.1 | 16.3 | 19.6 | 72 | 34 | 0.6 |
| Comparative | 62 | 26.3 | 22.5 | 12.5 | 15.6 | 45 | 95 | 2.3 |

TABLE 1-continued

|  | Average pore size(4 V/s)(μm) | CRC (g/g) | AUL (g/g) | WAUL (g/g) | Gel-AUL (g/g) | GBP (darcy) | Vortex time (s) | Rewetting amount (g/g) |
|---|---|---|---|---|---|---|---|---|
| Ex. 1 Comparative Ex. 2 | 0.8 | 31.2 | 18.4 | 11.2 | 15.4 | 56 | 78 | 1.8 |
| Comparative Ex. 3 | 1.2 | 30.7 | 21.2 | 12.8 | 16.2 | 18 | 84 | 1.7 |

The invention claimed is:

1. A super absorbent polymer comprising:
a base polymer powder containing a first crosslinked polymer of a water-soluble ethylene-based unsaturated monomer having an acidic group in which at least a part thereof is neutralized; and
a surface-crosslinked layer containing a second crosslinked polymer formed on the base polymer powder in which the first crosslinked polymer is additionally crosslinked via a surface crosslinking agent,
wherein the superabsorbent polymer is prepared by:
1) performing thermal polymerization or photopolymerization of a monomer composition comprising the water-soluble ethylene-based unsaturated monomer having the acidic group in which at least the part thereof is neutralized, a carbonate forming agent, an anionic surfactant and a polymerization initiator to form a hydrogel polymer, wherein the anionic surfactant is dioctyl sodium sulfosuccinate,
2) drying the hydrogel polymer,
3) pulverizing the dried polymer, and
4) performing surface cros slinking reaction of the pulverized polymer; and
wherein the super absorbent polymer has:
an average particle diameter of 300 μm to 600 μm,
CRC of 28 g/g to 35 g/g,
AUL (0.9 psi) of 18 g/g to 25 g/g,
10-min WAUL of 15 g/g to 25 g/g,
a gel bed permeability (GBP) for a physiological saline solution of 30 darcy or more,
5-min Gel-Vacuum AUL of 18 g/g to 25 g/g, and
a vortex time of 5 seconds to 50 seconds,
wherein
the WAUL is measured according to the following Equation 1:

$$WAUL(g/g)=[W_2(g)-W_1(g)]/W_0(g) \quad \text{[Equation 1]}$$

in Equation 1,
$W_0(g)$ is an initial weight(g) of the super absorbent polymer,
$W_1(g)$ is the total sum of a weight of the super absorbent polymer and a weight of the device capable of providing a load to the super absorbent polymer,
$W_2(g)$ is the total sum of a weight of the super absorbent polymer and a weight of the device capable of providing a load to the super absorbent polymer, after absorbing a physiological saline solution below 15 cm from the super absorbent polymer under a load (0.7 psi) for 10 minutes,
wherein the vortex time means the amount of time required until the vortex disappears after adding 2 g of a super absorbent polymer to 50 mL of physiological saline solution and then stirring the mixture at 600 rpm, and
wherein
the 5-min Gel-Vacuum AUL is measured according to the following Equation 5:

$$\text{5-min Gel-Vacuum AUL}(g/g)=[W_8(g)-W_7(g)]/W_0(g) \quad \text{[Equation 5]}$$

in Equation 5,
$W_0(g)$ is an initial weight(g) of the super absorbent polymer,
$W_7(g)$ is the total sum of the weight of the super absorbent polymer and the weight of the device capable of providing a load to the super absorbent polymer, and
$W_8(g)$ is the total sum of the weight of the super absorbent polymer and the weight of the device capable of providing a load to the super absorbent polymer, after absorbing a physiological saline solution to the super absorbent polymer under a load (0.3 psi) for 5 minutes and removing the remaining liquid with a vacuum device.

2. A super absorbent polymer comprising:
a base polymer powder containing a first crosslinked polymer of a water-soluble ethylene-based unsaturated monomer having an acidic group in which at least a part thereof is neutralized; and
a surface-crosslinked layer containing a second crosslinked polymer formed on the base polymer powder in which the first crosslinked polymer is additionally crosslinked via a surface crosslinking agent,
wherein the first crosslinked polymer is a porous polymer containing a plurality of pores on a micron (μm) scale,
wherein the superabsorbent polymer is prepared by:
1) performing thermal polymerization or photopolymerization of a monomer composition comprising the water-soluble ethylene-based unsaturated monomer having the acidic group in which at least the part thereof is neutralized, a carbonate forming agent, an anionic surfactant and a polymerization initiator to form a hydrogel polymer, wherein the anionic surfactant is dioctyl sodium sulfosuccinate,
2) drying the hydrogel polymer,
3) pulverizing the dried polymer, and
4) performing surface cros slinking reaction of the pulverized polymer;
wherein the super absorbent polymer has an average particle size of 300 μm to 600 μm, CRC of 28 g/g to 35 g/g, AUL (0.9 psi) of 18 g/g to 25 g/g, 5-min Gel-Vacuum AUL of 18 g/g to 25 g/g, and a vortex time of 5 seconds to 50 seconds,
wherein
the WAUL is measured according to the following Equation 1:

$$WAUL(g/g)=[W_2(g)-W_1(g)]/W_0(g) \quad \text{[Equation 1]}$$

in Equation 1,
$W_0(g)$ is an initial weight(g) of the super absorbent polymer, $W_1(g)$ is the total sum of a weight of the super absorbent polymer and a weight of the device capable of providing a load to the super absorbent polymer, $W_2(g)$ is the total sum of a weight of the super absorbent polymer and a weight of the device capable of providing a load to the super absorbent polymer, after absorbing a physiological saline solution below 15 cm from the super absorbent polymer under a load (0.7 psi) for 10 minutes, wherein the vortex time means the amount of time required until the vortex disappears after adding 2 g of a super absorbent polymer to 50 mL of physiological saline solution and then stirring the mixture at 600 rpm, wherein the 5-min Gel-Vacuum AUL is measured according to the following Equation 5:

$$\text{5-min Gel-Vacuum AUL}(g/g) = [W_8(g) - W_7(g)] / W_0(g) \quad \text{[Equation 5]}$$

in Equation 5, $W_0(g)$ is an initial weight(g) of the super absorbent polymer, $W_7(g)$ is the total sum of the weight of the super absorbent polymer and the weight of the device capable of providing a load to the super absorbent polymer, and $W_8(g)$ is the total sum of the weight of the super absorbent polymer and the weight of the device capable of providing a load to the super absorbent polymer, after absorbing a physiological saline solution to the super absorbent polymer under a load (0.3 psi) for 5 minutes and removing the remaining liquid with a vacuum device.

3. The super absorbent polymer according to claim 1, wherein the super absorbent polymer has a rewetting amount of 0.05 g/g to 1 g/g, which is measured according to the following Equation 6:

$$\text{Rewetting Amount } (g/g) = [W_{10}(g) - W_9(g)] / W_0(g) \quad \text{[Equation 6]}$$

in Equation 6, $W_0(g)$ is an initial weight(g) of the super absorbent polymer, $W_9(g)$ is an initial weight(g) of the second filter paper, $W_{10}(g)$ is a weight(g) of the second filter paper that has absorbed a liquid leaking out from the super absorbent polymer swelled for 2 minutes under a load (0.7 psi), after the super absorbent polymers have absorbed 25 times their weight in a physiological saline solution for a sufficient time under no load condition.

4. A method of preparing a super absorbent polymer according to claim 1:

1) performing thermal polymerization or photopolymerization of a monomer composition comprising a water-soluble ethylene-based unsaturated monomer having an acidic group in which at least a part thereof is neutralized, a carbonate forming agent, an anionic surfactant and a polymerization initiator to form a hydrogel polymer, wherein the anionic surfactant is dioctyl sodium sulfosuccinate, 2) drying the hydrogel polymer, 3) pulverizing the dried polymer, and 4) performing surface cros slinking reaction of the pulverized polymer.

5. The method of preparing a super absorbent polymer according to claim 4, wherein the carbonate foaming agent is at least one selected from the group consisting of sodium carbonate, sodium hydrogen carbonate, magnesium carbonate, calcium carbonate, potassium carbonate, and potassium hydrogen carbonate.

6. The method of preparing a super absorbent polymer according to claim 4, wherein the carbonate foaming agent is used in an amount of 0.01 to 0.1% by weight relative to the water-soluble ethylene-based unsaturated monomer.

7. The method of preparing a super absorbent polymer according to claim 4, wherein the anionic surfactant is a carboxylic acid salt, a sulfonic acid salt, or a phosphate, containing 6 to 18 carbon atoms.

8. The method of preparing a super absorbent polymer according to claim 4, wherein the anionic surfactant is used in an amount of 0.05 to 3% by weight relative to the water-soluble ethylene-based unsaturated monomer.

9. The method of preparing a super absorbent polymer according to claim 4, wherein the surface crosslinking reaction is carried out by using at least one surface cros slinking agent selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene carbonate, ethylene glycol, diethylene glycol, propylene glycol, triethylene glycol, tetraethylene glycol, propanediol, dipropylene glycol, polypropylene glycol, glycerin, polyglycerin, butanediol, heptanediol, hexanediol, trimethylolpropane, pentaerythritol, sorbitol, calcium hydroxide, magnesium hydroxide, aluminum hydroxide, iron hydroxide, calcium chloride, magnesium chloride, aluminum chloride and iron chloride.

10. The method of preparing a super absorbent polymer according to claim 4, wherein the surface crosslinking reaction is carried out by further using silica.

\* \* \* \* \*